US008334286B2

(12) United States Patent
Ghelardini et al.

(10) Patent No.: US 8,334,286 B2
(45) Date of Patent: Dec. 18, 2012

(54) SUBSTITUTED PYRROLO[1,2-A] PYRAZINES, COMPOSITIONS CONTAINING THESE, PROCESSES OF MAKING THESE, AND USES THEREOF

(75) Inventors: Carla Ghelardini, Pistoia (IT); Marisa Martinelli, Baranzate (IT); Carlo Parini, Baranzate (IT); Silvano Ronzoni, Gerenzano (IT)

(73) Assignee: Neurotune AG, Schlieren (CH)

( * ) Notice: Subject to any disclaimer, the term of this patent is extended or adjusted under 35 U.S.C. 154(b) by 0 days.

(21) Appl. No.: 12/918,718

(22) PCT Filed: Feb. 17, 2009

(86) PCT No.: PCT/CH2009/000064
§ 371 (c)(1),
(2), (4) Date: Oct. 4, 2010

(87) PCT Pub. No.: WO2009/103176
PCT Pub. Date: Aug. 27, 2009

(65) Prior Publication Data
US 2011/0015200 A1    Jan. 20, 2011

(30) Foreign Application Priority Data
Feb. 22, 2008  (EP) ..................... 08101879

(51) Int. Cl.
*A61K 31/495*    (2006.01)
(52) U.S. Cl. .......... 514/249; 544/349; 546/294
(58) Field of Classification Search ........... 514/249; 544/349; 546/294
See application file for complete search history.

(56) References Cited

U.S. PATENT DOCUMENTS 3,225,077 A   12/1965   Schaefer et al.
5,925,648 A   7/1999    Cooper et al.

FOREIGN PATENT DOCUMENTS

| EP | 1118612 | 7/2001 |
| JP | 05097819 | 4/1993 |
| WO | WO2005116009 A1 | 12/2005 |
| WO | WO2007028654 A1 | 3/2007 |
| WO | WO2007037743 | 4/2007 |

OTHER PUBLICATIONS

International Search Report of PCT/CH2009/000064 dated Apr. 7, 2009; 3 pages.
K. Hahn et al.; "A placebo-controlled trial of gabapentin for painful HIV-associated sensory neuropathies"; J Neurol (2004) 251: pp. 1260-1266.
"Recommendations for the Medical Management of Osteoarthritis of the Hip and Knee"; Arthritis & Rheumatism; vol. 43, No. 9, Sep. 2000; pp. 1905-1915.
G. Cavaletti et al.; "Effects of different schedules of oxaliplatin treatment on the peripheral nervous system of the rat"; European Journal of Cancer 37 (2001); pp. 2457-2463.
Richard M. Dubinsky, MD, et al.; "Reversible Axonal Neuropathy From the Treatment of Aids and Related Disorders With 2',3'-Dideoxycytidine (Ddc)"; Muscle & Nerve; Oct. 1989; pp. 856-860.
Janet Fernihough et al.; Pain related behaviour in two models of osteoarthritis in the rat knee; Pain 112 (2004); pp. 83-93.
Julie E. Hammack, et al.; "Phase III evaluation of nortriptyline for alleviation of symptoms of cis-platinum-induced peripheral neuropathy"; Pain 98 (2002); pp. 195-203.
K. Kieburtz, MD; "A randomized trial of amitriptyline and mexiletine for painful neuropathy in HIV infection"; American Academy of Neurology; 1998; pp. 1682-1688.
Fabien Marchand et al.; "Evidence for an antihyperalgesic effect of venlafaxine in vincristine-induced neuropathy in rat"; Brain Research 980 (2003); pp. 117-120.
Rosemary C. Polomano et al.; "A painful peripheral neuropathy in the rat produced by the chemotherapeutic drug, paclitaxel"; Pain 94 (2001); pp. 293-304.
Ravi D. Rao et al.; Efficacy of Lamotrigine in the Management of Chemotherapy-induced Peripheral Neuropathy—A Phase 3 Randomized, Double-blind, Placebo-contolled Trial, N01C3; American Cancer Society, 2008; pp. 2802-2808.
Ravi D. Rao et al.; Efficacy of Gabapentin in the Management of Chemotherapy-induced Peripheral Neuropathy—A Phase 3 Randomized, Double-Blind, Placebo-controlled, Crossover Trial (N00C3); American Cancer Society, 2007; pp. 2110-2118.
Stefan Van Den Branden et al.; Synthesis of Lactam and Ketone Precursors of 2,7-Substituted Octahydropyrrolo [1,2-a] pyrazines and Octahydro-2H-pyrido[1,2-a] pyrazines; J. Chem. Soc. Perkin Trans., 1992, pp. 1035-1042.
Dina Manetti et al.; "Design, Synthesis, and Preliminary Pharmacological Evaluation of 1,4-Diazabicyclo[4.3.0] nonan-9-ones as a New Class of Highly Potent Nootropic Agents"; J. Med. Chem. 2000, 43, pp. 1969-1974.

(Continued)

*Primary Examiner* — Douglas M Willis
(74) *Attorney, Agent, or Firm* — Abelman, Frayne & Schwab

(57) ABSTRACT

The invention refers to compounds of general formula (I) wherein the R groups are, independently, H, $C_{1-6}$alkyl, aryl, $CF_3$; Y is $CH_2$, C=O; X is bond, C=O, $SO_2$, or C=N—CN; m is 0, 1; n is 0, 1; A is a heterocycle, or a phenyl group optionally substituted as defined in the specification. The compounds are active on chronic pain conditions of different origin; they can be administered alone or with other drugs. Most of these compounds are new. The invention include a process to prepare said compounds, and pharmaceutical compositions suitable for their administration to a patient.

(I)

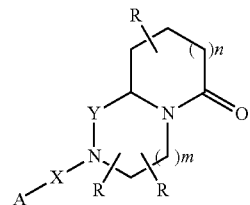

10 Claims, No Drawings

OTHER PUBLICATIONS

Justin C. McArthur; "Report from the 8th CROI: Sensory Neuropathy in HIV/AIDS"; The Hopkins HIV Report; May 2001; pp. 1-5.

Michael B. Smith, Jerry March; March's Advanced Organic Chemistry Reactions, Mechanisms, and Structure; Fifth Edition (2007); pp. 508, 509, 518-519, 523-524, 577, 704-705, 1187-1189, 1537.

Serena Scapecchi et al.; Structure-activity relationship studies on unifiram (DM232) and sunifiram (DM235), two novel and potent cognition enhancing drugs; Bioorganic & Medicinal Chemistry 12 (2004) 71-85.

European Search Report of EP 08101879.8 dated Sep. 4, 2008, pp. 1-8.

European Examination Report of EP 08101879.8 dated Aug. 31, 2010, pp. 1-6.

SUBSTITUTED PYRROLO[1,2-A] PYRAZINES, COMPOSITIONS CONTAINING THESE, PROCESSES OF MAKING THESE, AND USES THEREOF

FIELD OF THE INVENTION

The present invention relates to nitrogen-containing bicyclic compounds, a process for their preparation, pharmaceutical compositions containing them, and their use in medicine.

BACKGROUND OF THE INVENTION

Differently from acute pain, which plays an important physiological action alerting the organism towards an incoming danger or damage, chronic pain does not play any protective action.

Chronic pain may be divided in two main categories: chronic inflammatory pain and neuropathic pain. The latter is due to a direct lesion on the nervous pathways by the noxa, which can be infectious, metabolic, vascular or other. In chronic inflammatory pain the lesioned tissues release algogenic factors which in turn damage nervous terminals creating a vicious mechanism which maintains and potentiates the perception of pain.

Chronic pain, of both neuropathic and inflammatory origin, is an important epidemiologic aspect of a high unmet medical need condition, i.e. of a therapeutic area which at present needs remarkable improvements since poorly effective treatments and a plethora of important noxious side-effects are present.

An increasing number of patients suffers from iatrogenic neuropathic pain, induced by anti-tumor therapies used in modern oncology. In particular, taxol derived drugs, cisplatin and vincristine are among the drugs which more often induce the insurgence of painful neuropathies. Currently no effective and/or well tolerated treatments exist for this kind of pain. In fact classical potent analgesic drugs such as lamotrigine (Renno S. I. 2006 *J. Clin. Oncol. ASCO Annual Meeting Proceeding Part I* vol. 24, No 18S:8530), gabapentin (Wong G. Y. 2005 *J. Clin. Oncol. ASCO Annual Meeting Proceeding Part I* vol. 23, No 16S:8001) or nortriptyline (Hammack J. E. 2002, Pain 98:195-203) are absolutely not satisfactory on the basis of their therapeutic index.

Nucleoside analog reverse transcriptase inhibitors (ddC, d4T, AZT) are commonly used as antiviral drugs in the treatment of AIDS. These drugs often cause the insurgence of peripheral neuropathies with different degrees of severity after prolonged treatment. As in the case of chemotherapeutic agents, these symptoms may be so strong to induce shortening or suspension of these life-saving therapies. The patterns of these neuropathies are clearly different from those induced by the progression of AIDS; they are in fact characterized by the sudden onset of very intense burning discomfort in both hands and feet at about the tenth week of treatment. HIV-induced neuropathies, on the contrary, have a very slow progression (Dubinsky R. M. 1989, *Muscle Nerve* 12:856-860). As for chemotherapy-induced neuropathies, it is difficult to treat this kind of pain.

The tricycic antidepressant amitryptiline and the sodium channel blocker mexiletine, effective on various forms of painful peripheral neuropathies, did not show any significant effect on this kind of neuropathic pain (Kieburtz K. 1998 *Neurology* 51:1682-1688). "Gabapentin showed some efficacy in relieving HIV-associated sensory neuropathies Hanh K. 2004 J Neurol 251: 1260-1266.).

Other forms of neuropathic pain may be caused by viral infections. Postherpetic neuralgia, for instance, is caused by the reactivation, long after the infection, of the varicella-zoster virus. This kind of neuropathy is characterized by the development of strong mechanical allodynia, frequent loss of sensitivity towards thermal stimuli and spontaneous intermittent pain. The severity of pain may compromise the quality of life of patients suffering from this condition.

Cephalea is a kind of chronic pain of high epidemiologic relevance. When cephalea occurs in a paroxystic way, with recurrent episodes lasting from hours to days and is associated to general sickness, it is called hemicrania.

The current treatment for hemicrania entails the use of different kind of analgesic agents, from non-steroidal anti-inflammatory drugs (NSAIDs) to opioids, antihistaminic drugs and ergotamine derivatives. In the last decade triptan 5HT2 antagonists have been used; they are often able to block an attack at its insurgence, if promptly administered. All these methods show serious limits in terms of both efficacy and toxicity. In the most severe cases, in which painful attacks recur many times a week, a pre-emptive therapy with antiepileptic, beta blocker and antidepressant drugs is performed. The maximum result which can be achieved with these pre-emptive therapies is 50% reduction in the frequency and intensity of the painful attacks, but not their definitive remission.

Inflammatory pain is another form of chronic pain. It is caused by the release of mediators which either directly activate the nociceptors localized on primary afferents or lower their activation threshold, thus increasing their sensitivity to either painful or non-painful stimuli of different nature. Excited primary afferents may in turn release neurotransmitters which can stimulate immune cells recruited by the inflammatory process causing the release of additional inflammatory mediators.

This phenomenon, defined 'neurogenic inflammation', leads to an autoamplification of the symptomotology of the patient. Osteoarthritis is a particularly severe and painful form of this kind of pathology. Osteoarthritis is a form of degenerative arthritis causing the breakdown and eventual loss of the cartilage of one or more joints. The most common symptom related to this pathology is pain in the affected joint, which increases in proportion to the amount of use of the joint. As the disease progresses there is pain at rest and later nocturnal pain. Even if a certain correlation between pain and the extension of the damage at the joint has been demonstrated, the precise etiology of this kind of pain is still obscure; in fact, patients with relatively small damages at the joints suffer from very intense pain and viceversa; this finding suggests that it is not a merely inflammatory pain, but that a neuropathic component is present as well. Recommended treatments include NSAIDs, steroids and opioids, but the use of these drugs is associated with the insurgence of severe side-effects; in addition, their efficacy is not complete in many instances (2000 Arthritis Rheum. 43:1905-1915).

SUMMARY OF THE INVENTION

The present invention refers to compounds of general formula (I)

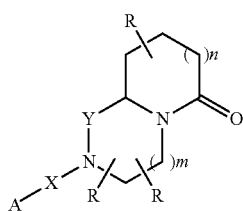

(I)

wherein:
the R groups are, independently, H, $C_{1-6}$alkyl, aryl, or $CF_3$;
Y is $CH_2$ or $C=O$
X is bond, $C=O$, $SO_2$, or $C=N-CN$
m is 0 or 1
n is 0 or 1
A is a heterocycle, or a group of formula:

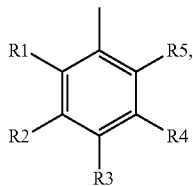

wherein:
R1, R2, R4 and R5 are, independently, H, halogen, $C_{1-6}$alkyl, $C_{1-6}$alkoxy, cyano, aryl, hydroxy, amino, $C_{1-6}$alkylamino, di($C_{1-6}$alkyl)amino, amino$C_{1-6}$alkyl, ($C_{1-6}$alkyl)amino-$C_{1-6}$alkyl, di($C_{1-6}$alkyl)amino$C_{1-6}$alkyl, carboxy or perhalo$C_{1-6}$alkyl; R3 is H, perhalo$C_{1-6}$alkyl, halogen, $C_{1-6}$alkyl, $C_{1-6}$alkoxy, cyano, carboxy, hydroxy, $C_{1-6}$alkylamino, di($C_{1-6}$alkyl)amino, amino$C_{1-6}$alkyl, ($C_{1-6}$alkyl)amino-$C_{1-6}$alkyl, or di($C_{1-6}$alkyl)amino$C_{1-6}$alkyl;
or two adjacent groups chosen among R1, R2, R3, R4, R5, may form a methylenedioxy or ethylenedioxy group. These compounds are useful in the treatment of any chronic pain conditions; in particular chronic pain of either neuropathic or inflammatory origin, including migraine and headache, epilepsy and dyskinesias associated with the treatment of Parkinson's disease with L-DOPA. Examples of specific diseases treated or prevented by the compounds of the invention are listed further on in this specification.

A large part of the compounds of formula (I) are new compounds: they represent per se a further object of the invention. The invention further includes a process for synthesizing these compounds and pharmaceutical composition for their administration to a patient.

DETAILED DESCRIPTION OF THE INVENTION

In the above formula (I), all "alkyl" groups can be indifferently linear or branched; said alkyl groups are preferably $C_{1-4}$alkyl groups, more preferably methyl or ethyl. All "aryl" groups are preferably $C_{5-10}$aryl groups, in particular phenyl and naphthyl. The term "heterocycle" means saturated and unsaturated, single or fused heterocyclic rings, and comprising up to four heteroatoms, chosen among oxygen, sulphur and nitrogen.

All alkyl, aryl or heterocyclic groups may be optionally substituted one or more times by e.g. halogen, $C_{1-6}$alkyl, $C_{1-6}$alkoxy, hydroxy, amino, $C_{1-6}$alkylamino, di($C_{1-6}$alkyl)amino, amino$C_{1-6}$alkyl, ($C_{1-6}$alkyl)amino$C_{1-6}$alkyl, di($C_{1-6}$alkyl)amino$C_{1-6}$alkyl, carboxy, cyano or perhalo$C_{1-6}$alkyl.

The R groups shown in formula (I) may be attached at any position of the rings upon which they are drawn: thus the upper drawn ring contains one R group, and the lower drawn ring contains two R groups, with all R being independently chosen among the above defined meanings. In particular on the pyrazine ring, the two R groups may be attached to different ring members, as well as to the same ring member: in the latter case, where both R represent an identical $C_{1-6}$alkyl, they form a geminal substituent, e.g. gem-dimethyl.

Preferably, R is H or $C_{1-4}$alkyl; more preferably, R is H, methyl or ethyl; even more preferably, R is H.

Preferably, X is bond, $C=O$, $SO_2$; more preferably, X is bond or $SO_2$.

Preferably, A is aryl, 2-pyridyl, 3-pyridyl, 4-pyridyl; more preferably, A is aryl substituted with halogen, cyano, trifluoromethyl, methyl; even more preferably, A is 2-fluorophenyl and 3-fluorophenyl.

Specific compounds of formula (I) according to the present invention are the following:
(S)-(−)2-(2-fluorophenylsulfonyl)hexahydropyrrolo[1,2-a]pyrazin-6(7H)-one;
(S)-(−)2-(3-fluorophenylsulfonyl)hexahydropyrrolo[1,2-a]pyrazin-6(7H)-one;
(R)-(+)2-(2-fluorophenylsulfonyl)hexahydropyrrolo[1,2-a]pyrazin-6(7H)-one;
(R)-(+)2-(3-fluorophenylsulfonyl)hexahydropyrrolo[1,2-a]pyrazin-6(7H)-one;
(R)-(+)-2-(3,4-difluorophenylsulfonyl)hexahydropyrrolo[2-a]pyrazin-6(7H)-one;
(R)-(+)-2-(o-tolylsulfonyl)hexahydropyrrolo[1,2-a]pyrazin-6(7H)-one;
(R)-(+)-2-(m-tolylsulfonyl)hexahydropyrrolo[1,2-a]pyrazin-6(7H)-one;
(R)-(+)-2-(2-(trifluoromethyl)phenylsulfonyl)hexahydropyrrolo[1,2-a]pyrazin-6(7H)-one;
(R)-(+)-2-(3-(trifluoromethyl)phenylsulfonyl)hexahydropyrrolo[1,2-a]pyrazin-6(7H)-one;
(R)-(+)-2-(4-(trifluoromethyl)phenylsulfonyl)hexahydropyrrolo[1,2-a]pyrazin-6(7H)-one;
(R)-2-(6-oxohexahydropyrrolo[1,2-a]pyrazin-2(1H)-ylsulfonyl)benzonitrile;
(R)-3-(6-oxohexahydropyrrolo[1,2-a]pyrazin-2(1H)-ylsulfonyl)benzonitrile;
(R)-(+)-4-(6-oxohexahydropyrrolo[1,2-a]pyrazin-2(1H)-ylsulfonyl)benzonitrile;
(R)-2-(2-methoxyphenylsulfonyl)hexahydropyrrolo[1,2-a]pyrazin-6(7H)-one,
(R)-2-(3-methoxyphenylsulfonyl)hexahydropyrrolo[1,2-a]pyrazin-6(7H)-one,
(R)-2-(pyridin-3-ylsulfonyl)hexahydropyrrolo[1,2-a]pyrazin-6(7H)-one;
(R)-2-(pyridin-2-ylsulfonyl)hexahydropyrrolo[1,2-a]pyrazin-6(7H)-one;
(S)-2-(2-fluorobenzoyl)hexahydropyrrolo[1,2-a]pyrazin-6(7H)-one;
(S)-2-(3-fluorobenzoyl)hexahydropyrrolo[1,2-a]pyrazin-6(7H)-one;

(R)-2-(2-fluorobenzoyl)hexahydropyrrolo[1,2-a]pyrazin-6 (7H)-one;
(R)-2-(3-fluorobenzoyl)hexahydropyrrolo[1,2-a]pyrazin-6 (7H)-one;
(S)-(−)-2-(3-methylisoxazole-5-carbonyl)hexahydropyrrolo [1,2-a]pyrazin-6(7H)-one;
2-(2-Fluoro-benzenesulfonyl)-octahydro-pyrido[1,2-a] pyrazin-6-one,
2-p-Tolyl-tetrahydro-pyrrolo[1,2-a]pyrazine-1,6-dione;
2-(3-Fluoro-benzenesulfonyl)-octahydro-pyrido[1,2-a] pyrazin-6-one;
2-(2-Fluoro-benzenesulfonyl)-3,3-dimethyl-hexahydro-pyrrolo[1,2-c]imidazol-5-one;
3,3-Dimethyl-2-p-tolyl-tetrahydro-pyrrolo[1,2-c]imidazole-1,5-dione The compounds of formula (I) can exhibit stereoisomerism because of the presence of chiral atoms and/or multiple bonds. The present invention therefore extends to stereoisomers of the compounds of formula (I), including racemates and mixtures where the enantiomers are present in any proportions, enantiomers, diastereoisomers and geometric isomers.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

The compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labelled reagent.

The compounds of formula (I) are new compounds, with the exceptions specified below. The new compounds represent per se a further embodiment of the present invention and are included as such within its scope. The new compounds are described by formula (I) as above defined, with the proviso that:
(i) when, simultaneously, Y is CH$_2$, X is C═O or SO$_2$, m is 1, n is 0 and R1, R2, R4 and R5 are all hydrogen, then R3 is not H, F, Cl, OCH$_3$, CH$_3$;
(ii) when simultaneously, Y is CH$_2$, X is C═O, m is 1, n is 0 or 1, and R1, R4 and R5 (or R1, R2 and R5) are all hydrogen, then R2 with R3 (or R3 with R4) does not form a methylenedioxy or ethylenedioxy group.
(iii) when simultaneously, Y is CH$_2$ and m and n are both 1, then the group A-X taken together is not 4-fluorobenzenesulfonyl or unsubstituted benzoyl.

The compounds disclaimed by (i) are known from EP-A-1118612; those disclaimed by (ii) and (iii) are known from *Bioorg. Med. Chem.*, 12 (2004), 71-85. The present invention also provides processes for preparing the compounds of formula (I).

The compounds of formula (I) in which X is C═O or SO$_2$, hereinafter referred as formula (Ia), can be prepared as described in Scheme 1, reacting a compound of formula (II) with a compound of formula (III), where R, Y, n, m and A are as defined for formula (I) and W is halogen.

Scheme 1

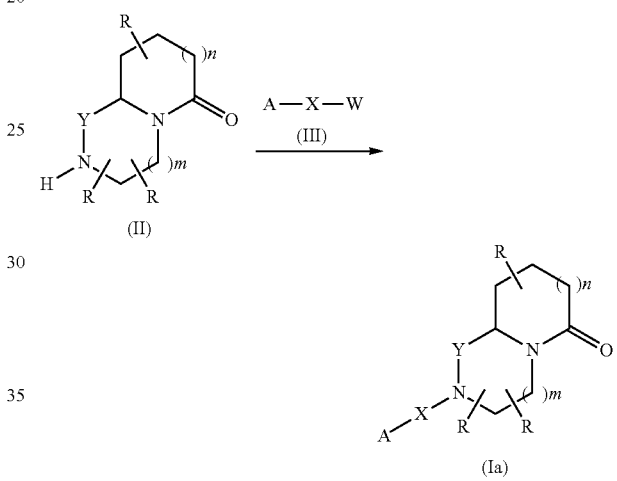

In a typical procedure, a compound of formula (II) is dissolved in a suitable solvent, such as e.g. dichloromethane, acetonitrile, dimethylformamide or mixtures thereof, in the presence of a suitable organic or inorganic base, such as e.g. triethylamine or potassium carbonate, then a solution of a compound of formula (III) in a suitable solvent, such as e.g. dichloromethane, acetonitrile, dimethylformamide or mixtures thereof, is added to the preceding reaction mixture at a suitable temperature, typically between 0° C. and ambient temperature. After stirring for a suitable period of time, typically between 1 and 24 hours at a suitable temperature, typically between 0° C. and ambient temperature, the solvent is evaporated, the residue is taken up with water and a suitable solvent, such as for example ethyl acetate or dichloromethane. After extraction, the organic phase is collected, dried with, for example, sodium sulfate and the solvent is removed by evaporation. The crude product may be purified, if necessary, by conventional purification methods such as flash chromatography, trituration, crystallization or preparative HPLC.

The compounds of formula (I) in which X is a bond, hereinafter referred as formula (Ib), can be prepared according to Scheme 2, reacting a compound of formula (II) with a compound of formula (IV), where R, Y, m, n and A are as defined for formula (I) and W is as defined above.

Scheme 2

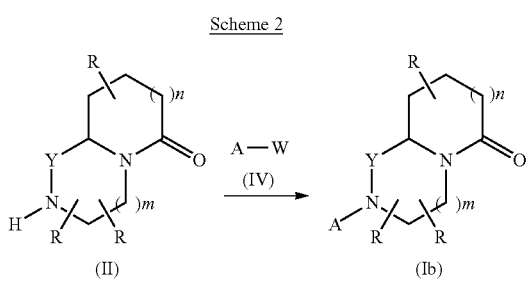

In a typical procedure, a compound of formula (II) is dissolved in a suitable solvent, such as e.g. dimethylformamide, then a compound of formula (IV) is added, together with CuI and a suitable base, such as for example potassium carbonate and the resulting mixture is stirred at a suitable temperature, typically between room temperature and reflux temperature, for a suitable time, typically between 1 and 16 hours. The solvent is evaporated and the resulting residue is triturated with a suitable solvent, such as, for example, ethyl acetate, then the residual solids are filtered off, the organic solution is washed with water or a saturated aqueous sodium chloride solution, then it is dried with, for example, sodium sulfate and the solvent is evaporated. The crude product may be purified, if necessary, by conventional purification methods such as flash chromatography, trituration, crystallization or preparative HPLC.

The compounds of formula (I) in which X is a group C=N—CN, hereinafter referred as formula (Ic), may be prepared as described in Scheme 3, reacting a compound of formula (II) with a compound of formula (V), where R, Y, m, n and A have the meanings defined for formula (I) and Q is a linear or branched $C_{1-4}$alkyl, under conditions described in U.S. Pat. No. 5,925,648.

Scheme 3

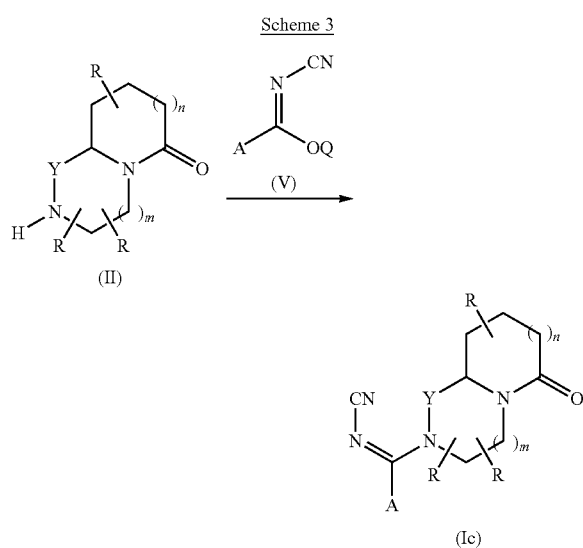

The compounds of formula (II) in which n is 0, Y is $CH_2$ and R and m are as defined for formula (I), hereinafter referred as formula (IIa) can be prepared according to the reaction sequence illustrated in Scheme 4, in which a compound of formula (VI) is converted in the corresponding methanesulfonate (VII) (step A), which is then reacted in step B with a compound of formula (VIII) to give a compound of formula (IX), which is in turn converted into the corresponding methanesulfonate (X) in step C and cyclised to compound (XI) in step D. Finally, debenzylation in step E yields compounds of formula (IIa).

Scheme 4

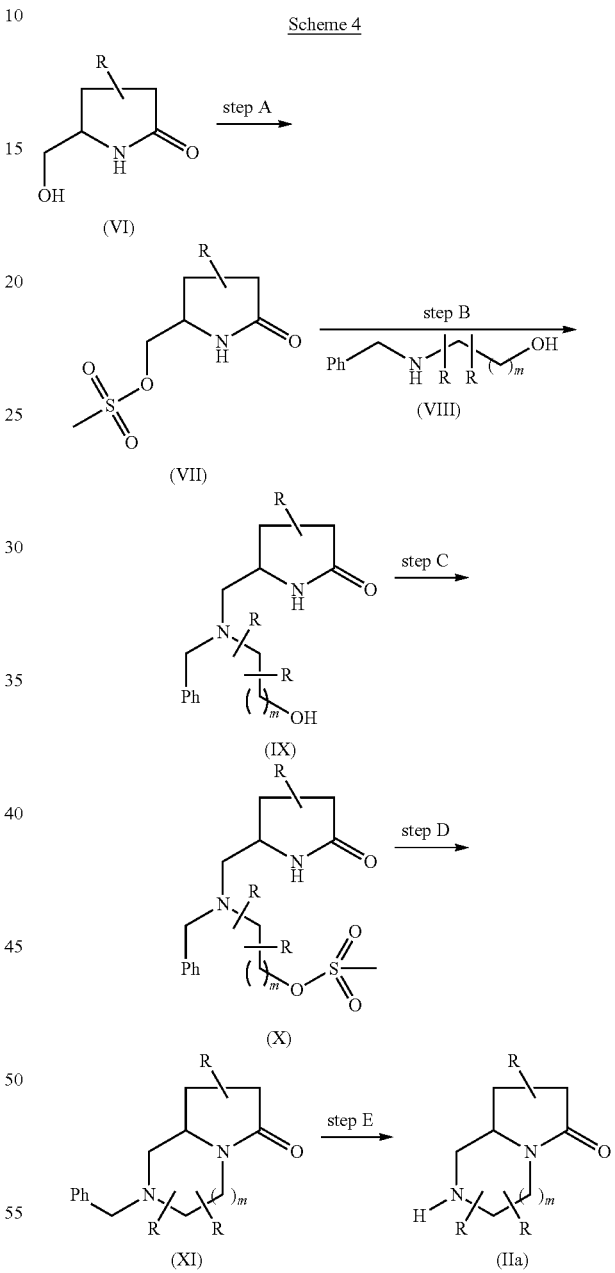

Step A is typically conducted dissolving a compound of formula (VI) in a suitable solvent such as e.g. ethanol-free chloroform, then adding at a suitable temperature, typically between 0° C. and room temperature, a suitable base such as triethylamine, followed by methanesulfonyl chloride, stirring the reaction mixture for a suitable period of time, typically between 1 and 12 h, at a suitable temperature, typically between 0° C. and room temperature. The reaction mixture is then diluted with a suitable solvent, such as for example dichloromethane, and washed with an aqueous solution of a suitable base, such as a saturated aqueous solution of sodium bicarbonate. The organic solution is then dried with for example sodium sulfate and evaporated. The crude-product may be purified, if necessary, by conventional purification methods such as flash chromatography, trituration, crystallization or preparative HPLC, yielding a compound of formula (VII) to be processed in step B.

Step B is typically performed by heating a compound of formula (VII) with a compound of formula (VIII) in a microwave oven at a suitable temperature, typically between 50° C. and 150° C., preferably at 130° C., for a suitable period of time, typically between 10 and 60 minutes, preferably 40-45 minutes, then partitioning the residue between water and a suitable solvent such as dichloromethane, washing the organic phase with a saturated sodium chloride solution, drying it over e.g. sodium sulfate and evaporating the solvent. The crude product may be purified, if necessary, by conventional purification methods such as flash chromatography, trituration, crystallization or preparative HPLC, yielding a compound of formula (IX) to be processed in step C.

Step C can be carried out following the conditions reported above for step A, yielding a compound of formula (X) to be processed in step D.

Step D is typically carried out by dissolving a compound of formula (X) in a suitable solvent, such as e.g. acetonitrile or tetrahydrofuran or mixtures thereof, then adding a suitable base such as, for example, sodium hydride, at a suitable temperature, typically between 0° C. and room temperature. After stirring at a suitable temperature, typically between 0° C. and room temperature, for a suitable time, typically between 1 and 24 hours, preferably between 4 and 16 hours, the solvent is removed and the residue is taken up with water and extracted with a suitable solvent, such as dichloromethane or ethyl acetate. The organic phase may be washed with a saturated sodium chloride solution, then it is dried with, for example, sodium sulfate and then evaporated. The crude product may be purified, if necessary, by conventional purification methods such as flash chromatography, trituration, crystallization or preparative HPLC, yielding a compound of formula (XI) to be processed in step E.

Step E is a typical debenzylation reaction, which can be performed e.g. in phase-transfer conditions, dissolving a compound of formula (XI) in a suitable solvent such as an alcohol, e.g. methanol, adding a suitable hydrogen source such as ammonium formate, followed by a suitable catalyst, such as palladium on carbon, and then heating the reaction mixture at a suitable temperature, typically reflux temperature, for a suitable time, typically between 1 and 8 hours, preferably between 2 and 3 hours. The catalyst is filtered off and the solvent evaporated. The crude product may be purified, if necessary, by conventional purification methods such as flash chromatography, trituration, crystallization or preparative HPLC, yielding a compound of formula (IIa).

The compounds of formula (II) in which n is 1, Y is $CH_2$ and R and m are as defined for formula (I), hereinafter referred as formula (IIb), may be prepared as described in Scheme 5, in which a compound of formula (XII) is reacted in step F with a compound of formula (XIII), where R, W and Q are as defined above, to give a compound of formula (XIV) which is converted in step G into a compound of formula (IIb).

Scheme 5

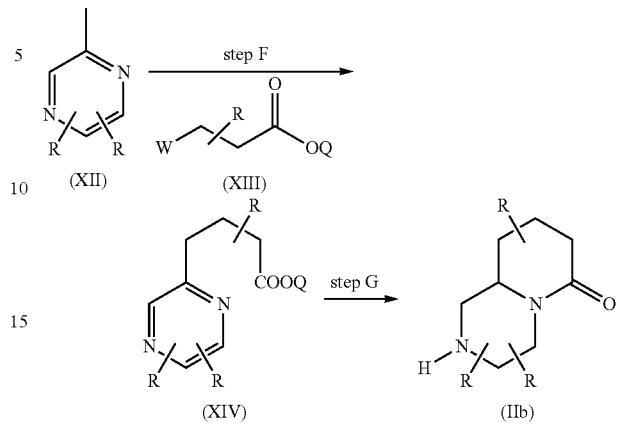

Step F may be typically performed dissolving a compound of formula (XII) in a suitable solvent such as tetrahydrofuran, and then adding this solution to a solution of a suitable base in a suitable solvent, such as a solution of lithium diisopropylamide in tetrahydrofuran, under an inert atmosphere, such as a nitrogen or argon atmosphere, at a suitable temperature, typically between −78° C. and −20° C. After stirring for a suitable time, typically between 5 and 60 minutes, a solution of a compound of formula (XIII) in a suitable solvent such as tetrahydrofuran, is added to the preceding solution and stirring is continued for a suitable time, typically between 2 and 20 hours, at a suitable temperature, typically between −78° C. and room temperature; the reaction is then quenched with e.g. a saturated ammonium chloride solution, then it is extracted with a suitable solvent, such as ethyl acetate. The organic phase is dried with e.g. sodium sulfate and the solvent is evaporated. The crude product may be purified, if necessary, by conventional purification methods such as flash chromatography, trituration, crystallization or preparative HPLC, yielding a compound of formula (XIV) to be processed in step G.

Step G is a typical hydrogenation reaction, which can be conducted dissolving a compound of formula (XIV) in a suitable solvent such as ethanol, then adding a suitable catalyst such as palladium on carbon, and then hydrogenating the reaction mixture at a suitable hydrogen pressure, typically between 20 and 50 psi, for a suitable period of time, typically between 1 and 24 hours. The catalyst is filtered off, the solvent is evaporated and the crude product may be purified, if necessary, by conventional purification methods such as flash chromatography, trituration, crystallization or preparative HPLC, yielding a compound of formula (IIb).

The compounds of formula (II) in which n is 0, Y is C=O and R and m are as defined for formula (I), hereinafter referred as formula (IIc), may be prepared as described in Scheme 6, converting a compound of formula (XV) into a compound of formula (XVI) (step H), where Q is as defined above, then reacting said compound of formula (XVI) with a compound of formula (XVII) in step I to give a compound of formula (XVIII) which is converted in step J into a compound of formula (IIc).

Scheme 6

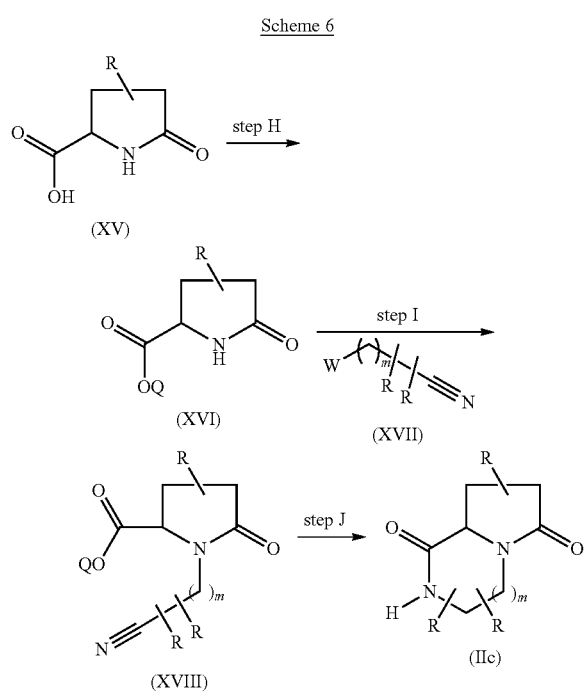

Step H is a typical esterification reaction, which may be performed for example dissolving the compound of formula (XV) in a suitable alcoholic solvent of formula Q-OH, e.g. methanol or ethanol, then adding an acidic cation exchange resin (e.g. Amberlyst® 15) and stirring the resulting mixture for a suitable time, typically between 1 and 24 hours, at a suitable temperature, typically between room and reflux temperature; after filtering off the insoluble materials and evaporating the solvent, a compound of formula (XVI) is obtained, which may be purified, if necessary, by conventional purification methods such as flash chromatography, trituration, crystallization or preparative HPLC, before being processed in step I. Step I is typically performed dissolving a compound of formula (XVI) in a suitable solvent, such as for example acetonitrile, then adding a suitable base such as, e.g., sodium hydride, at a suitable temperature, typically between −10° C. and room temperature, then after stirring for a suitable time, typically between 15 min and 2 hours, a solution of a compound of formula (XVII) in a suitable solvent such as acetonitrile, is added to the preceding reaction mixture and stirring is continued for a suitable period of time, typically between 1 and 24 hours, at a suitable temperature, typically between −10° C. and room temperature. The solvent is evaporated, the residue is partitioned between water and a suitable solvent such as, e.g., ethyl acetate, the organic phase is dried with e.g. sodium sulfate and evaporated. The crude product may be purified, if necessary, by conventional purification methods such as flash chromatography, trituration, crystallization or preparative HPLC, yielding a compound of formula (XVIII) to be processed in step J.

Step J is a typical hydrogenation reaction, which can be performed by dissolving the compound of formula (XVIII) in a suitable solvent, such as e.g. methanol, then adding a suitable catalyst such as platinum oxide, an hydrogenating the resulting reaction mixture at a suitable hydrogen pressure, typically between 20 and 50 psi, for a suitable time, typically between 1 and 24 hours. After filtering off the catalyst and evaporating the solvent, the crude product may be purified, if necessary, by conventional purification methods such as flash chromatography, trituration, crystallization or preparative HPLC, yielding a compound of formula (IIc).

The compounds of formulae (III), (IV), (VI), (VIII), (XII), (XIII), (XV) and (XVII) are either known or commercially available compounds, or may be prepared as described in reference texts of synthetic methodology, such as March's Advanced Organic Chemistry, Sixth Edition (2007), Wiley Interscience.

The compounds of formula (V) may be prepared as described e.g. in U.S. Pat. No. 3,225,077.

According to the present invention, the compounds of formula (I) can be used in the treatment of any chronic pain conditions, particularly those of neuropathic or inflammatory origin; chronic pain may be originated e.g. by neuropathies deriving from nerve injury or compression, diabetic polineuropathies, post-herpetic neuralgia, or may be the side effect of treatments with other drugs. Examples of chronic pain-causing treatments are those with chemotherapeutic agents (where the chemotherapeutic agent is e.g. taxol and derivatives thereof, cisplatin, oxaliplatin or vinca alkaloids in oncological patients), antibacterial agents (such as e.g. metronidazole or isoniazid), antiviral agents (particularly nucleoside reverse transcriptase inhibitors, e.g. ddC, d4T or AZT in HIV-patients). Other examples of chronic pain conditions treatable with the invention are those associated to osteoarthritis, phantom limb, multiple sclerosis or other inflammatory autoimmune diseases, neuropathies, fibromyalgia, carpal and tarsal tunnel syndromes, headache, migraine and complex regional pain syndromes (CRPS).

The compounds of the invention are also useful for the treatment of epilepsy and dyskinesias associated with the treatment of Parkinson's disease with L-DOPA.

According to the present invention, the compounds of formula (I) may be administered as such or in association with any other active principle useful for the treatment or prevention of the above mentioned diseases. Non-limiting examples of other active principles to be used in association with compounds of the invention are e.g. gabapentin or pregabalin for the treatment of chronic pain.

It is also part of the invention the administration of compounds of formula (I) in association with active principles which present as side effect the insurgence of chronic pain, in particular antitumor and antiviral drugs; non-limiting examples of such drugs are taxol, vincristine, cisplatin, oxaliplatin among the antitumor agents, nucleoside reverse transcriptase inhibitors such as ddC, d4T, AZT among the antiviral drugs.

The compound of formula (I) can also be used in advance to a chemotherapeutic treatment, so as to prevent the development of chronic pain. In this case the treatment with compound of the invention is started before the chemotherapeutic treatment and possibly continues jointly therewith.

The compounds of formula (I) are also useful in treating possible chemotherapy-induced peripheral neurotoxicity (CIPN) symptoms developing after conclusion of the treatment with chemotherapeutic drugs; in this case the treatment with compounds of formula (I) is started (or continued) after conclusion of the chemotherapeutic treatment.

The compounds of formula (I) can be prepared in the forms of salts or hydrates. Suitable salts are pharmaceutically acceptable salts. Suitable hydrates are pharmaceutically acceptable hydrates.

The therapeutic regimen for the different clinical syndromes must be adapted to the type and seriousness of the pathology or pathologies to be treated, taking into account also the route of administration, the form in which the compound is administered and the age, weight and conditions of the subject involved. The compounds of the invention can be administered at doses ranging e.g. from about 10 to about 1500 mg/day.

The invention encompasses pharmaceutical compositions of compounds of formula (I) useful for the above mentioned treatments. The amounts of the active principle, expressed in mg/day, are those cited above Compounds of the invention may be pharmaceutically formulated according to known methodologies. The various pharmaceutical compositions may be selected according to the needs of the treatment.

Such compositions can be prepared by mixing and can be suitably adapted for oral or parenteral administration, and as such, can be administered in the form of tablets, capsules, oral preparations, powders, granules, pellets, liquid solutions for injection or infusion, suspensions or suppositories.

Tablets and capsules for oral administration are usually supplied in dosage units and may contain conventional excipients such as binders, fillers, diluents, tabletting agents, lubricants, detergents, disintegrants, colorants, flavors and wetting agents. Tablets may be coated in accordance to methods well known in the art.

Suitable fillers include for example cellulose, mannitol, lactose and similar agents. Suitable disintegrants include starch, polyvinylpyrrolidone and starch derivatives such as sodium starch glycolate. Suitable lubricants include, for example, magnesium stearate. Suitable wetting agents include for example sodium lauryl sulfate.

These solid oral compositions can be prepared with conventional mixing, filling or tabletting methods. The mixing operations can be repeated to disperse the active agent in compositions containing large quantities of fillers. These operations are conventional.

The oral liquid compositions can be provided in the form of, for example, aqueous or oily suspensions, solutions, emulsions, syrups or elixirs or in the form of a dry product to be reconstituted with water or with a suitable liquid carrier at the time of use. The liquid compositions can contain conventional additives such as suspending agents, for example sorbitol, syrup, methylcellulose, gelatin, hydroxyethylcellulose, carboxymethylcellulose, aluminium stearate gel or hydrogenated edible fats, emulsifying agents, for example lecithin, sorbitan monooleate, or acacia; non aqueous carriers (which can include edible oil) for example almond oil, fractionated coconut oil, oily esters such a glycerin esters, propylene glycol or ethyl alcohol; preservatives, for example methyl or propyl p-hydroxybenzoate or sorbic acid and if desired, conventional flavours or colorants. Oral formulations also include conventional sustained release formulations, such as tablets or granules with enteric coating.

For parenteral administration, fluid dosage units can be prepared containing the active compounds and a sterile carrier. The active compounds, depending on the carrier and concentration, can be suspended or dissolved. The parenteral solutions are normally prepared by dissolving the compound in a carrier and sterilizing by filtration, before filling suitable vials or ampoules and sealing. Adjuvants such as local anaesthetics, preservatives and buffering agents can be advantageously dissolved in the carrier. In order to increase stability, the composition can be frozen after filling the vial and the water removed under vacuum. The parenteral suspensions are prepared essentially in the same way, with the difference that the active compounds can be suspended rather than dissolved in the carrier, and can be sterilized by exposure to ethylene oxide prior to being suspended in the sterile carrier. A surfactant or humectant can be advantageously included to facilitate uniform distribution of the compound of the invention.

A further method of administration for the compound of the invention refers to a topic treatment. Topic formulations may contain for example ointments, creams, lotions, gels, solutions, pastes and/or may contain liposomes, micelles and/or microspheres.

A further method of administration for the compounds of the invention is transdermal delivery. Typical transdermal formulations include conventional aqueous and non-aqueous vectors, such as creams, oil, lotions or pastes or may be in the form of membranes or medicated patches.

As is the common practise, the compositions are normally accompanied by written or printed instructions, for use in the treatment concerned.

Examples of the present invention are provided in what follows, purely for illustrative and non-limiting purposes.

EXPERIMENTAL PART

Chemistry

Description 1

(+)-Methanesulfonic acid
(S)-5-oxo-pyrrolidin-2-ylmethyl ester

To a solution of commercially available (S)-(+)-5-(hydroxymethyl)pyrrolidin-2-one (2 g, 17.36 mmol) in ethanol-free $CHCl_3$ (60 ml), triethylamine (TEA) (2.63 g, 26.04 mmol) and methanesulfonyl chloride (2.38 g, 20.84 mmol) were added dropwise at 0° C. The mixture was left stirring at room temperature for 3 hours, then it was diluted with dichloromethane (DCM) (60 ml) and washed with a saturated aqueous solution of $NaHCO_3$ (3×30 ml). After drying ($Na_2SO_4$) the solvent was removed under reduced pressure and the residue was purified by flash chromatography (DCM/MeOH 9/1 respectively) to give the title compound as a pale yellow solid (2.2 g, 65% yield).

m.p. 72-74° C.
$[\alpha]_D^{25}$=+18.54 (c=1, 96% EtOH)
$^1$H-NMR (300 MHz, $CDCl_3$, δ ppm): 6.21 (br. s., 1 H), 4.27 (dd, 1 H), 4.09 (dd, 1 H), 3.95-4.05 (m, 1 H), 3.07 (s, 3 H), 2.24-2.47 (m, 3 H), 1.80-1.94 (m, 1 H).
UPLC/MS: 194 ($MH^+$).

Description 2

(S)-(+)-5-((Benzyl(2-hydroxyethyl)amino)methyl)
pyrrolidin-2-one

A mixture of (+)-methanesulfonic acid (S)-5-oxo-pyrrolidin-2-ylmethyl ester (500 mg, 2.59 mmol) and 2-(benzylamino)ethanol (1.56 g, 10.36 mmol) was heated at 130° C. in a microwave oven (Personal Chemistry Emrys™ Optimizer) for 40 minutes. The residue was partitioned between water and DCM, the organic phase was washed with brine, dried ($Na_2SO_4$) and evaporated under vacuum. The crude was purified by flash chromatography (DCM/MeOH from 95/5 to 90/10 respectively) to afford the title compound as yellow oil (620 mg, 96% yield).

$[\alpha]_D^{25}$=+38.54 (c=1, 96% EtOH).
$^1$H-NMR (300 MHz, $CDCl_3$, δ ppm): 7.76 (br. s., 1 H), 7.19-7.43 (m, 5 H), 3.62-3.88 (m, 3 H), 3.37-3.62 (m, 3 H), 2.73-2.85 (m, 1 H), 2.47-2.63 (m, 3 H), 2.21-2.42 (m, 2 H), 2.02-2.21 (m, 1 H), 1.48-1.66 (m, 1 H).
UPLC/MS: 249.1 ($MH^+$).

Description 3

Methanesulfonic acid 2-[benzyl-((S)-5-oxo-pyrrolidin-2-ylmethyl)-amino]-ethyl ester To a solution of (S)-(+)-5-((benzyl(2-hydroxyethyl)amino)methyl)pyrrolidin-2-one (3.5 g, 14.1 mmol) in ethanol-free CHCl$_3$ (55 ml), TEA (2.85 g, 28.22 mmol) and methanesulfonyl chloride (3.23 g, 28.22 mmol, in 10 ml of CHCl$_3$) were added at 0° C. The mixture was allowed to warm to room temperature and left stirring for 20 hours, then it was diluted with DCM (60 ml) and washed with a saturated solution of NaHCO$_3$ (3×50 ml). After drying (Na$_2$SO$_4$) and removal of the solvent, the crude was purified by flash chromatography (DCM/abs EtOH/Petroleum Ether/33% NH$_4$OH/Et$_2$O 300/180/900/9.9/360 respectively) to afford the title compound (2.9 g, 63% yield).

UPLC/MS: 327.1 (MH$^+$).

Description 4

(S)-(−)-2-Benzylhexahydropyrrolo[1,2-a]pyrazin-6(7H)-one

Methanesulfonic acid 2-[benzyl-((S)-5-oxo-pyrrolidin-2-ylmethyl)-amino]-ethyl ester (2.9 g, 8.89 mmol) was dissolved in a mixture of CH$_3$CN/THF (1/1, 40 ml) and then 60% NaH (462 mg, 11.56 mmol) was added portionwise at room temperature, under a nitrogen atmosphere. After stirring for 16 hours, the solvent was removed under vacuum and the residue was taken up with water and extracted with DCM. The organic phase was washed with brine, dried (Na$_2$SO$_4$) and evaporated under vacuum. The residue was purified by flash chromatography (DCM/abs EtOH/Petroleum Ether/33% NH$_4$OH/Et$_2$O 300/180/900/9.9/360 respectively) to afford the title compound as a yellow oil (2 g, 97% yield).

$[\alpha]_D^{25}$=−55.54 (c=1, 96% EtOH)

$^1$H-NMR (300 MHz, CDCl$_3$, δ ppm): 7.26-7.40 (m, 5 H), 3.98-4.07 (m, 1 H), 3.60-3.73 (m, 1 H), 3.61 (d, 1 H), 3.52 (d, 1H), 2.80-3.02 (m, 3 H), 2.34-2.45 (m, 2 H), 1.94-2.22 (m, 2 H), 1.75 (dd, 1 H), 1.50-1.66 (m, 1 H).

UPLC/MS: 231.1 (MH$^+$).

Description 5

(S)-(−)-Hexahydropyrrolo[1,2-a]pyrazin-6(7H)-one

A mixture of (S)-(−)-2-benzylhexahydropyrrolo[1,2-a]pyrazin-6(7H)-one (2 g, 8.69 mmol), ammonium formate (3.83 g, 60.8 mmol) and 10% Pd/C (500 mg) in MeOH (90 ml) was refluxed for 2 hours. After cooling to room temperature, the catalyst was filtered off and the solvent evaporated under vacuum. The residue was purified by flash chromatography (DCM/MeOH/32% NH$_4$OH, 70/30/3 respectively) to afford the title compound as a colourless oil (1 g, 82% yield).

$[\alpha]_D^{25}$=−31.46 (c=1, 96% EtOH).

$^1$H-NMR (300 MHz, CDCl$_3$, δ ppm): 4.02 (ddd, 1 H), 3.45-3.63 (m, 1 H), 3.17 (dd, 1 H), 2.98-3.07 (m, 1 H), 2.74-2.89 (m, 1 H), 2.61 (td, 1 H), 2.28-2.47 (m, 3 H), 2.08-2.25 (m, 1 H), 1.48-1.68 (m, 1 H).

Description 6

(−)-Methanesulfonic acid (R)-5-oxo-pyrrolidin-2-ylmethyl ester

To a solution of commercially available (R)-(−)-5-(hydroxymethyl)pyrrolidin-2-one (5 g, 43.4 mmol) in ethanol-free CHCl$_3$ (150 ml), Et$_3$N (6.9 g, 68.3 mmol) and methanesulfonyl chloride (5.96 g, 52.0 mmol) were added dropwise at 0° C. The mixture was left stirring at room temperature for 3 hours, then it was diluted with DCM and washed with a saturated aqueous solution of NaHCO$_3$. After drying (Na$_2$SO$_4$) the solvent was removed under reduced pressure and the residue was purified by flash chromatography (DCM/MeOH 95/5 respectively) to give the title compound as a pale yellow solid (5.9 g, 70% yield).

$[\alpha]_D^{25}$=−19.16 (c=1, 96% EtOH). $^1$H-NMR spectra is identical to that of (S)-(+)-analogue.

Description 7

(R)-(−)-5-((Benzyl(2-hydroxyethyl)amino)methyl)pyrrolidin-2-one

A mixture of (−)-methanesulfonic acid (R)-5-oxo-pyrrolidin-2-ylmethyl ester (10.53 g, 54.5 mmol) and 2-(benzylamino)ethanol (32.58 g, 215.5 mmol) was heated at 130° C. in a microwave oven (Personal Chemistry Emrys™ Optimizer) for 45 minutes. The residue was partitioned between water and DCM, the organic phase was washed with brine, dried (Na$_2$SO$_4$) and evaporated under vacuum. The crude was purified by flash chromatography (DCM/MeOH 95/5 respectively) to afford the title compound as yellow oil (13.3 g, 98% yield).

$[\alpha]_D^{25}$=−40 (c=1, 96% EtOH). $^1$H-NMR spectra is identical to that of (S)-(+)-analogue.

Description 8

Methanesulfonic acid 2-[benzyl-((R)-5-oxo-pyrrolidin-2-ylmethyl)-amino]-ethyl ester To a solution of (R)-(−)-5-((benzyl(2-hydroxyethyl)amino)methyl)pyrrolidin-2-one (2.4 g, 9.67 mmol) in ethanol-free CHCl$_3$ (80 ml), TEA (1.95 g, 19.34 mmol) and methansulfonyl chloride (2.21 g, 19.34 mmol) were added at 0° C. The mixture was allowed to warm to room temperature and left stirring for 6 hours, then it was diluted with DCM (80 ml) and washed with a saturated solution of NaHCO$_3$. After drying (Na$_2$SO$_4$) and removal of the solvent, the crude was purified by flash chromatography (DCM/abs EtOH/Petroleum Ether/33% NH$_4$OH/Et$_2$O 300/180/900/9.9/360 respectively) to afford the title compound (2.3 g, 73% yield).

Description 9

(R)-(+)-2-Benzylhexahydropyrrolo[1,2-a]pyrazin-6(7H)-one

Methanesulfonic acid 2-[benzyl-((R)-5-oxo-pyrrolidin-2-ylmethyl)-amino]-ethyl ester (3.5 g, 10.74 mmol) was dissolved in CH$_3$CN (20 ml) and then 60% NaH (558 mg, 13.96 mmol) was added portionwise at room temperature. After stirring for 4 hours, the solvent was removed under vacuum and the residue was treated with water and extracted with ethyl acetate. The organic phase was washed with brine, dried (Na$_2$SO$_4$) and evaporated under vacuum. The residue was purified by flash chromatography (DCM/abs EtOH/Petroleum Ether/33% NH$_4$OH/Et$_2$O 300/180/900/9.9/360 respectively) to afford the title compound as yellow oil (2.1 g, 85% yield).

$[\alpha]_D^{25}$=+55.5 (c=1, 96% EtOH). $^1$H-NMR spectra is identical to that of (S)-(−)-analogue.

Description 10

(R)-(+)-Hexahydropyrrolo[1,2-a]pyrazin-6(7H)-one

A mixture of (R)-(+)-2-benzylhexahydropyrrolo[1,2-a]pyrazin-6(7H)-one (2 g, 8.69 mmol), ammonium formate (3.83 g, 60.8 mmol) and 10% Pd/C (550 mg) in MeOH (90 ml) was refluxed for 3 hours. After cooling to room temperature, the catalyst was filtered off and the solvent evaporated under vacuum. The residue was purified by flash chromatography (DCM/MeOH/32% NH$_4$OH, 70/30/3 respectively) to afford the title compound as a colourless oil (1.1 g, 90% yield).

$[\alpha]_D^{25}$=+28.04 (c=1, 96% EtOH). $^1$H-NMR spectra is identical to that of (S)-(−)-analogue.

Description 11

4-Pyrazin-2-yl-butyric acid ethyl ester

Butyllithium (1.6 M in hexane solution, 10 ml, 16 mmol) was added dropwise to a solution of diisopropylamine (2.25 ml, 16 mmol) in anhydrous THF (50 ml) at −20° C. under a nitrogen atmosphere. The mixture was stirred at −20° C. for 30 minutes and after cooling at −70° C. a solution of 2-methyl-pyrazine (1.47 ml, 16 mmol) in THF (10 ml) was added dropwise. After 15 minutes, a solution of 3-bromo-propionic acid ethyl ester (2.54 ml, 19.2 mmol) in THF (10 ml) was added and the mixture maintained at −70° C. for 2 hours and then stirred at room temperature overnight. The reaction was then quenched with a saturated solution of NH$_4$Cl and extracted with ethyl acetate, the organic phase was dried (Na$_2$SO$_4$) and evaporated. The residue was purified by flash chromatography (hexane/ethyl acetate from 9/1 to 1/1 respectively) to give the title compound (1 g, 33% yield).

UPLC/MS: 195.1 (MH$^+$).

Description 12

Octahydro-pyrido[1,2-a]pyrazin-6-one

4-Pyrazin-2-yl-butyric acid ethyl ester (1 g, 5.14 mmol) was dissolved in abs. EtOH (50 ml) and hydrogenated over 10% Pd/C (200 mg) at 50 psi for 20 hours. After filtration, the solvent was removed under vacuum and the residue was purified by flash chromatography (DCM/MeOH/32% NH$_4$OH from 95/5/0.5 to 90/10/1 respectively) to afford the title compound (454 mg, 57% yield).

UPLC/MS: 155.1 (MH$^+$).

Description 13

5-Oxo-pyrrolidine-2-carboxylic acid methyl ester

A mixture of 5-oxo-pyrrolidine-2-carboxylic acid (5 g, 38.7 mmol) and Amberlyst® 15 (5 g) in MeOH (50 ml) was refluxed for 20 hours. After cooling, the reaction was filtered and the solvent removed under vacuum to afford the title compound (4.9 g, 90% yield) that was used without further purification in the next step.

Description 14

1-Cyanomethyl-5-oxo-pyrrolidine-2-carboxylic acid methyl ester

To a solution of 5-oxo-pyrrolidine-2-carboxylic acid methyl ester (3 g, 21 mmol) in CH$_3$CN (60 ml), 60% NaH (863 mg, 22 mmol) was added at 0° C. After stirring for 30 minutes, a solution of 2-bromoacetonitrile (2.59 g, 21 mmol) in CH$_3$CN (10 ml) was added dropwise. After warming at room temperature, and stirring for 20 hours, the solvent was evaporated under reduced pressure. The residue was partitioned between water and ethyl acetate, the organic layer was washed with brine, dried (Na$_2$SO$_4$) and evaporated. The residue was purified by flash chromatography (from DCM to DCM/MeOH 95/5 respectively) to afford the title compound as a pale yellow oil (1.1 g, 29% yield).

$^1$H-NMR (300 MHz, CDCl$_3$, δ ppm): 4.76 (d, 1 H), 4.31-4.43 (m, 1 H), 4.01 (d, 1 H), 3.83 (s, 3 H), 2.38-2.60 (m, 3 H), 2.11-2.32 (m, 1 H).

Description 15

Tetrahydro-pyrrolo[1,2-a]pyrazine-1,6-dione

1-Cyanomethyl-5-oxo-pyrrolidine-2-carboxylic acid methyl ester (1.1 g, 6.04 mmol) was dissolved in MeOH (30 ml) and hydrogenated over PtO$_2$ (200 mg) at 20 psi for 24 hours. After filtration of the catalyst, the solvent was removed under vacuum and the residue triturated with iPrOH to afford the title compound as a white powder (580 mg, 62% yield).

m.p.: 197° C.-199° C.

$^1$H-NMR (300 MHz, CDCl$_3$, δ ppm): 6.26 (br. s., 1 H), 4.06-4.33 (m, 2 H), 3.43-3.58 (m, 1 H), 3.32-3.43 (m, 1 H), 3.08-3.27 (m, 1 H), 2.36-2.62 (m, 3 H), 2.00-2.26 (m, 1 H).

MS (ESI Pos, 3.2 KV, 25V, 350° C.): 155.06 (MH$^+$).

Examples 1-2

General Procedure for the Preparation of (S)-2-(arylsulfonyl)hexahydropyrrolo[1,2-a]pyrazin-6(7H)-one To a solution of (S)-(−)-hexahydropyrrolo[1,2-a]pyrazin-6(7H)-one (compound of Description 5, 50 mg, 0.36 mmol) and TEA (43 mg, 0.43 mmol) in DCM (1.5 ml), a solution of aryl sulfonyl chloride (0.36 mmol, in 1 ml of CH$_3$CN) was added dropwise at 0° C. After stirring the solution at room temperature for 20 hours, the solvent was removed and the residue was treated with water and extracted with ethyl acetate. The organic phase was washed with brine, dried (Na$_2$SO$_4$) and evaporated under vacuum. The crude was triturated with iPr$_2$O and filtered to give the desired compound as a solid. Analytical data and yields for examples 1-2 are reported in Table 1.

TABLE 1

Analytical data and yields for examples 1-2

| Ex. No. | Structure | Chemical name | Analytical data and yield |
|---|---|---|---|
| 1 | 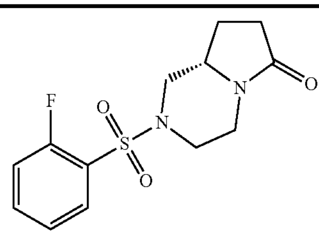 | (S)-(−)2-(2-fluorophenyl sulfonyl)hexahydro pyrrolo[1,2-a]pyrazin-6(7H)-one | $^1$H-NMR (300 MHz, CDCl3, δ ppm): 7.88 (ddd, 1 H), 7.53-7.70 (m, 1 H), 7.32 (ddd, 1 H), 7.25 (ddd, 1 H), 3.98-4.19 (m, 2 H), 3.81-3.96 (m, 1 H), 3.64-3.81 (m, 1 H), 2.97 (ddd, 1 H), 2.55 (dddd, 1 H), 2.32 (dddd, 4 H), 1.51-1.70 (m, 1 H). MS (ESI Pos, 3.2KV, 25V, 350° C.): 299.11 (MH$^+$). $[\alpha]_D^{25}$ = −40.30 (c = 1, DCM). m.p.: 142° C.-144° C. Yield: 66% (white powder). |

TABLE 1-continued

Analytical data and yields for examples 1-2

| Ex. No. | Structure | Chemical name | Analytical data and yield |
|---|---|---|---|
| 2 | 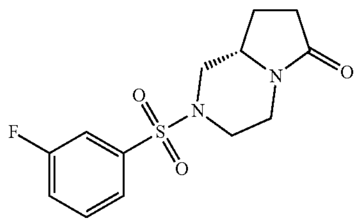 | (S)-(−)2-(3-fluorophenyl sulfonyl)hexahydro pyrrolo[1,2-a]pyrazin-6(7H)-one | $^1$H-NMR (300 MHz, CDCl3, δ pm): 7.51-7.63 (m, 2 H), 7.43-7.51 (m, 1 H), 7.29-7.41 (m, 1 H), 4.11 (ddd, 1 H), 3.94 (ddd, 1 H), 3.81 (dddd, 1 H), 3.67-3.77 (m, 1 H), 2.89-3.06 (m, 1 H), 2.17-2.50 (m, 4 H), 2.04 (dd, 1 H), 1.50-1.68 (m, 1 H). MS (ESI Pos, 3.2KV, 25V, 350° C.): 299.11 (MH$^+$). $[α]_D^{25}$ = −45.10 (c = 1, DCM). m.p.: 177° C.-179° C. Yield: 71% (white powder). |

Examples 3-17

General Procedure for the Preparation of (R)-2-(aryl or heteroarylsulfonyl)hexahydropyrrolo[1,2-a]pyrazin-6(7H)-one To a solution of (R)-(+)-hexahydropyrrolo[1,2-a]pyrazin-6(7H)-one (compound of Description 10, 50 mg, 0.36 mmol) and TEA (43 mg, 0.43 mmol) in DCM (1.5 ml), a solution of aryl or heteroaryl sulfonyl chloride (0.36 mmol, in 1 ml of CH$_3$CN) was added dropwise at 0° C. After stirring the solution at room temperature for 20 hours, the solvent was removed and the residue was treated with water and extracted with ethyl acetate. The organic phase was washed with brine, dried (Na$_2$SO$_4$) and evaporated. The crude was triturated with iPr$_2$O and filtered to give the desired compound as a solid. Analytical data and yields for examples 3-17 are reported in Table 2.

TABLE 2

Analytical data and yields for examples 3-17

| Ex. No | Structure | Chemical name | Analytical data and yield |
|---|---|---|---|
| 3 | 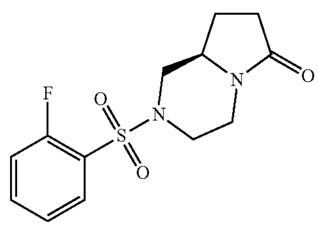 | (R)-(+)2-(2-fluorophenyl sulfonyl)hexahydro pyrrolo[1,2-a]pyrazin-6(7H)-one | $^1$H-NMR (300 MHz, CDCl3, δ ppm): 7.88 (ddd, 1 H), 7.54-7.74 (m, 1 H), 7.29-7.38 (m, 1 H), 7.19-7.28 (m, 1 H), 3.99-4.18 (m, 2 H), 3.88 (dt, 1 H), 3.63-3.80 (m, 1 H), 2.97 (td, 1 H), 2.50-2.64 (m, 1 H), 2.15-2.49 (m, 4 H), 1.56-1.70 (m, 1 H). MS (ESI Pos, 3.2KV, 25V, 350° C.): 299.24 (MH$^+$). $[α]_D^{25}$ = +36.34 (c = 1, DCM). m.p.: 136° C.-137° C. Yield: 71% (white powder). |
| 4 | 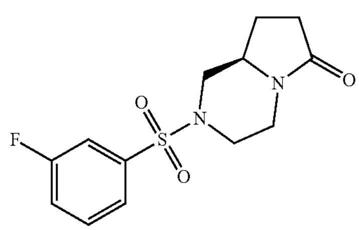 | (R)-(+)2-(3-fluorophenyl sulfonyl)hexahydro pyrrolo[1,2-a]pyrazin-6(7H)-one | $^1$H-NMR (300 MHz, CDCl3, δ ppm): 7.52-7.64 (m, 2 H), 7.44-7.52 (m,1 H), 7.30-7.41 (m, 1 H), 4.12 (ddd, 1 H), 3.95 (ddd, 1 H), 3.82 (dddd, 1 H), 3.66-3.78 (m, 1 H), 2.87-3.05 (m, 1 H), 2.16-2.54 (m, 4 H), 1.96-2.12 (m, 1 H), 1.56-1.70 (m, 1 H). MS (ESI Pos, 3.2KV, 25V, 350° C.): 299.24 (MH$^+$). $[α]_D^{25}$ = +43.50 (c = 1, DCM). m.p.: 179° C.-180° C. Yield: 79% (white powder). |
| 5 | 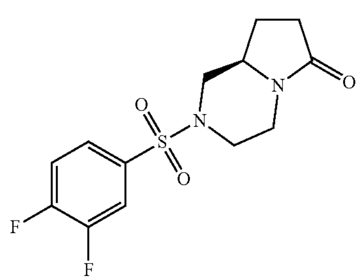 | (R)-(+)-2-(3,4-difluorophenyl sulfonyl)hexahydro pyrrolo[1,2-a]pyrazin-6(7H)-one | $^1$H-NMR (300 MHz, CDCl3, δ ppm): 7.48-7.70 (m, 2 H), 7.37 (ddd, 1 H), 4.12 (ddd, 1 H), 3.93 (ddd, 1 H), 3.77-3.85 (m, 1 H), 3.67-3.77 (m, 1 H), 2.86-3.11 (m, 1 H), 2.18-2.50 (m, 4 H), 2.05 (dd, 1 H), 1.49-1.67 (m, 1 H). MS (ESI Pos, 3.2KV, 25V, 350° C.): 317.22 (MH$^+$). $[α]_D^{25}$ = +39.60 (c = 1, DCM). m.p.: 208° C.-209° C. Yield: 55% (white powder). |

TABLE 2-continued

Analytical data and yields for examples 3-17

| Ex. No | Structure | Chemical name | Analytical data and yield |
|---|---|---|---|
| 6 | 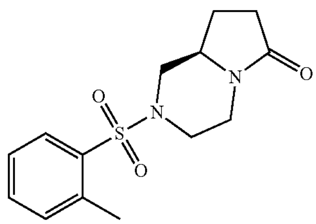 | (R)-(+)-2-(o-tolyl sulfonyl)hexahydro pyrrolo[1,2-a]pyrazin-6(7H)-one | $^1$H-NMR (300 MHz, CDCl3, δ ppm): 7.91 (dd, 1 H), 7.45-7.55 (m, 1 H), 7.30-7.40 (m, 2 H), 4.09 (ddd, 1 H), 3.91 (ddd, 1 H), 3.61-3.81 (m, 2 H), 2.86-3.02 (m , 1 H), 2.63 (ddd, 1 H), 2.63 (s, 3 H), 2.33-2.46 (m, 3 H), 2.13-2.31 (m, 1 H), 1.50-1.69 (m, 1 H). <br> MS (ESI Pos, 3.2KV, 25V, 350° C.): 295.20 (MH$^+$). <br> $[α]_D^{25}$ = +32.62 (c = 1, DCM). <br> m.p.: 68° C.-70° C. <br> Yield: 59% (white powder). |
| 7 | 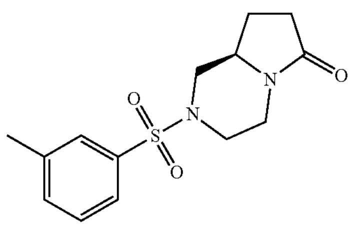 | (R)-(+)-2-(m-tolyl sulfonyl)hexahydro pyrrolo[1,2-a]pyrazin-6(7H)-one | $^1$H-NMR (300 MHz, CDCl3, δ ppm): 7.49-7.60 (m, 2 H), 7.39-7.47 (m, 2 H), 4.02-4.17 (m, 1 H), 3.93 (ddd, 1 H), 3.80 (dddd, 1 H), 3.67-3.80 (m, 1 H), 2.84-3.10 (m, 1 H), 2.46 (s, 3 H), 2.15-2.49 (m, 4 H), 1.99 (dd, 1 H), 1.44-1.68 (m, 1 H). <br> MS (ESI Pos, 3.2KV, 25V, 350° C.): 295.20 (MH$^+$). <br> $[α]_D^{25}$ = +41.70 (c = 1, DCM). <br> m.p.: 133° C.-134° C. <br> Yield: 71% (white powder). |
| 8 | 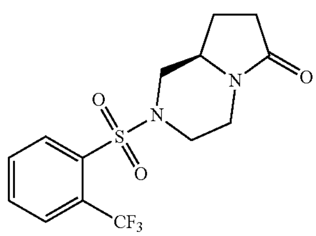 | (R)-(+)-2-(2-(trifluoro methyl)phenylsulfonyl) hexahydropyrrolo [1,2-a]pyrazin-6(7H)-one | $^1$H-NMR (300 MHz, CDCl3, δ ppm): 8.08-8.25 (m, 1 H), 7.85-8.00 (m, 1 H), 7.66-7.81 (m, 2 H), 4.09 (ddd, 1 H), 4.00 (ddd, 1 H), 3.78 (dddd, 1 H), 3.65-3.77 (m, 1 H), 2.88-3.05 (m, 1 H), 2.71 (ddd, 1 H), 2.48 (dd, 1 H), 2.38-2.46 (m, 2 H), 2.15-2.32 (m, 1 H), 1.52-1.69 (m, 1 H). <br> MS (ESI Pos, 3.2KV, 25V, 350° C.): 349.21 (MH$^+$). <br> $[α]_D^{25}$ = +29.76 (c = 1, DCM). <br> m.p.: 157° C.-158° C. <br> Yield: 69% (white powder). |
| 9 | 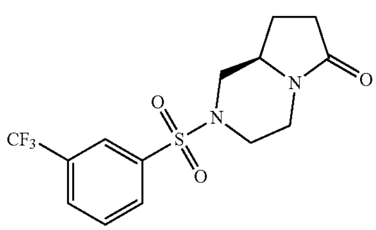 | (R)-(+)-2-(3-(tifluoro methyl)phenylsulfonyl) hexahydropyrrolo [1,2-a]pyrazin-6(7H)-one | $^1$H-NMR (300 MHz, CDCl3, δ ppm): 8.00-8.05 (m, 1 H), 7.93-8.00 (m, 1 H), 7.87-7.93 (m, 1 H), 7.73 (dd, 1 H), 4.12 (ddd, 1 H), 3.97 (ddd, 1 H), 3.80-3.89 (m, 1 H), 3.68-3.80 (m, 1 H), 2.90-3.06 (m, 1 H), 2.18-2.51 (m, 4 H), 2.05 (dd, 1 H), 1.49-1.66 (m, 1 H). <br> MS (ESI Pos, 3.2KV, 25V, 350° C.): 349.21 (MH$^+$). <br> $[α]_D^{25}$ = +40.08 (c = 1, DCM). <br> m.p.: 172° C.-174° C. <br> Yield: 72% (white powder). |
| 10 | 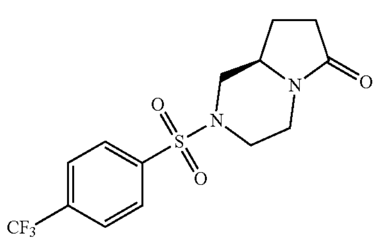 | (R)-(+)-2-(4-(trifluoro methyl)phenylsulfonyl) hexahydropyrrolo [1,2-a]pyrazin-6(7H)-one | $^1$H-NMR (300 MHz, CDCl3, δ ppm): 7.90 (m, 2 H), 7.84 (m, 2 H), 4.12 (ddd, 1 H), 3.97 (ddd, 1 H), 3.84 (dddd, 1 H), 3.66-3.80 (m, 1 H), 2.86-3.11 (m, 1 H), 2.19-2.50 (m, 4H), 2.05 (dd, 1 H), 1.47-1.68 (m, 1 H). <br> MS (ESI Pos, 3.2KV, 25V, 350° C.): 349.07 (MH$^+$). <br> $[α]_D^{25}$ = +35.46 (c = 1, DCM). <br> m.p.: 226° C.-227° C. <br> Yield: 72% (white powder). |
| 11 | 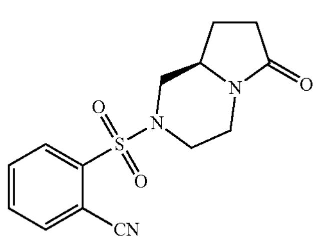 | (R)-2-(6-oxohexahydro pyrrolo[1,2-a]pyrazin-2(1H)-ylsulfonyl) benzonitrile | $^1$H-NMR (300 MHz, CDCl3, δ ppm): 8.05-8.13 (m, 1 H), 7.88-7.95 (m, 1 H), 7.68-7.84 (m, 2 H), 4.05-4.21 (m, 2 H), 3.80-3.89 (m, 1 H), 3.74-3.80 (m, 1 H), 2.97 (td, 1 H), 2.66 (td, 1 H), 2.35-2.53 (m, 3 H), 2.17-2.35 (m, 1 H), 1.57-1.70 (m, 1 H). <br> MS (ESI Pos, 3.2KV, 25V, 350° C.): 306 (MH$^+$). <br> m.p.: 198° C.-199° C. <br> Yield: 30% (white powder). |

TABLE 2-continued

Analytical data and yields for examples 3-17

| Ex. No | Structure | Chemical name | Analytical data and yield |
|---|---|---|---|
| 12 | 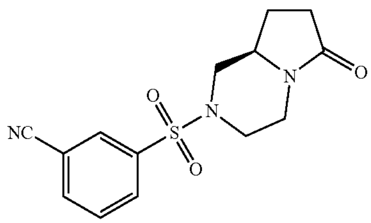 | (R)-3-(6-oxohexahydro pyrrolo[1,2-a]pyrazin-2(1H)-ylsulfonyl) benzonitrile | $^1$H-NMR (300 MHz, CDCl3, δ ppm): 8.06 (t, 1 H), 7.99 (ddd, 1 H), 7.88-7.95 (m, 1 H), 7.65-7.77 (m, 1 H), 4.06-4.19 (m, 1 H), 3.97 (ddd, 1 H), 3.83 (dddd, 1 H), 3.67-3.80 (m, 1 H), 2.91-3.07 (m, 1 H), 2.19-2.51 (m, 4 H), 2.07 (dd, 1 H), 1.51-1.67 (m, 1 H).<br>MS (ESI Pos, 3.2KV, 25V, 350° C.): 306.2 (MH$^+$).<br>m.p.: 180° C.-181° C.<br>Yield: 46% (white powder). |
| 13 | 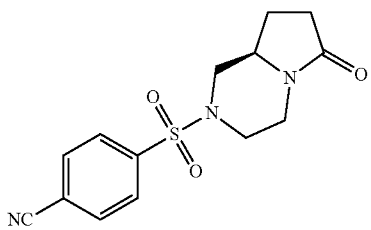 | (R)-(+)-4-(6-oxohexahydro pyrrolo[1,2-a]pyrazin-2(1H)-ylsulfonyl) benzonitrile | $^1$H-NMR (300 MHz, CDCl$_3$, δ ppm): 7.78-7.94 (m, 4 H), 4.02-4.20 (m,1 H), 3.94 (ddd, 1 H), 3.77-3.88 (m, 1 H), 3.64-3.77 (m, 1 H), 2.85-3.05 (m, 1 H), 2.15-2.48 (m, 4 H), 2.05 (dd, 1 H), 1.45-1.66 (m, 1 H).<br>MS (ESI Pos, 3.2KV, 25V, 350° C.): 306.18 (MH$^+$).<br>$[α]_D^{25}$ = +48.32 (c = 1, DCM).<br>m.p.: 242° C.-243° C.<br>Yield: 61% (white powder). |
| 14 | 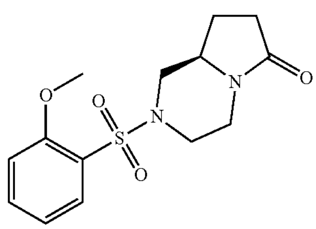 | (R)-2-(2-methoxyphenyl sulfonyl)hexahydro pyrrolo[1,2-a]pyrazin-6(7H)-one | $^1$H-NMR (300 MHz, DMSO-d6, δ ppm): 7.75 (dd, 1 H), 7.64 (ddd, 1 H), 7.25 (d, 1 H), 7.10 (dt, 1 H), 3.89 (s, 3 H), 3.82-3.91 (m, 1 H), 3.73-3.81 (m, 1 H), 3.65-3.73 (m, 1 H), 3.46-3.60 (m, 1 H), 2.66-2.82 (m, 1 H), 2.42-2.56 (m, 1 H), 2.29-2.42 (m, 1 H), 2.00-2.29 (m, 3 H), 1.41-1.62 (m, 1 H).<br>MS (ESI Pos, 3.2KV, 25V, 350° C.): 311.06 (MH$^+$).<br>Yield: 65% (white powder). |
| 15 | 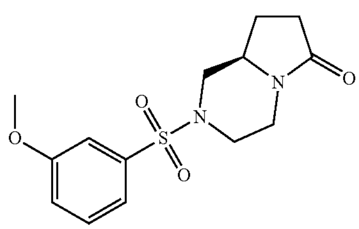 | (R)-2-(3-methoxyphenyl sulfonyl)hexahydro pyrrolo[1,2-a]pyrazin-6(7H)-one | $^1$H-NMR (300 MHz, DMSO-d6, δ ppm): 7.57 (dd, 1 H), 7.24-7.37 (m, 2 H), 7.17-7.22 (m, 1 H), 3.85 (s, 3 H), 3.74-3.93 (m, 2 H), 3.51-3.74 (m, 2 H), 2.75-2.90 (m, 1 H), 1.95-2.26 (m, 5 H), 1.43-1.65 (m, 1 H).<br>MS (ESI Pos, 3.2KV, 25V, 350° C.): 311.10 (MH$^+$).<br>m.p.: 144° C.-145° C.<br>Yield: 40% (white powder). |
| 16 | 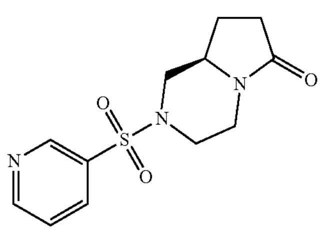 | (R)-2-(pyridin-3-yl sulfonyl)hexahydro pyrrolo[1,2-a]pyrazin-6(7H)-one | $^1$H-NMR (300 MHz, DMSO-d6, δ ppm): 8.92 (d, 1 H), 8.89(dd, 1 H), 8.17 (ddd, 1 H), 7.69 (ddd, 1 H), 3.77-3.93 (m, 2 H), 3.67-3.76 (m, 1 H), 3.55-3.67 (m, 1 H), 2.84 (td, 1 H), 2.02-2.31 (m, 5 H), 1.43-1.61 (m, 1 H).<br>MS (ESI Pos, 3.2KV, 25V, 350° C.): 282.12 (MH$^+$).<br>m.p.: 165° C.-166° C.<br>Yield: 42% (white powder). |
| 17 | 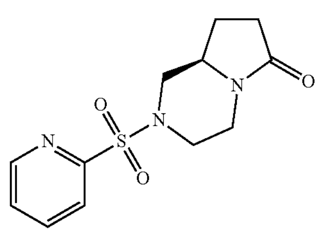 | (R)-2-(pyridin-2-yl sulfonyl)hexahydro pyrrolo[1,2-a]pyrazin-6(7H)-one | $^1$H-NMR (300 MHz, DMSO-d6, δ ppm): 8.76 (ddd, 1 H), 8.13 (td, 1 H), 7.95 (dt, 1 H), 7.72 (ddd, 1 H), 3.81-3.95 (m, 2 H), 3.76 (dddd, 1 H), 3.49-3.67 (m, 1 H), 2.81 (ddd, 1 H), 2.58 (ddd, 1 H), 2.45 (dd, 1 H), 2.02-2.34 (m, 3 H), 1.38-1.66 (m, 1 H).<br>MS (ESI Pos, 3.2KV, 25V, 350° C.): 282.08 (MH$^+$).<br>Yield: 40% (white powder). |

Examples 18-21

General Procedure for the Preparation of (S) and (R) 2-(arylcarbonyl)hexahydropyrrolo[1,2-a]pyrazin-6(7H)-one To a solution of (S)-(−) or (R)-(+)-hexahydropyrrolo[1,2-a]pyrazin-6(7H)-one (compounds of Descriptions 5 or 10 respectively, 30 mg, 0.21 mmol) and TEA (25 mg, 0.25 mmol) in DCM (1 ml), a solution of benzoyl chloride (0.21 mmol) in DCM (0.5 ml) was added dropwise at 0° C. After stirring the solution at room temperature for 4 hours, the solvent was removed under vacuum and the residue was treated with water and the product extracted with ethyl acetate. The organic phase was washed with brine, dried ($Na_2SO_4$) and evaporated. The crude was triturated with $iPr_2O$ and filtered to give the desired compound as a solid. Analytical data and yields for examples 18-21 are reported in Table 3.

TABLE 3

Analytical data and yields for examples 18-21

| Ex. No. | Structure | Chemical name | Analytical data and yield |
|---|---|---|---|
| 18 | 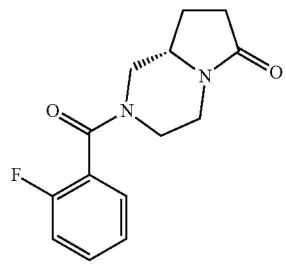 | (S)-2-(2-fluorobenzoyl) hexahydropyrrolo [1,2-a]pyrazin-6(7H)-one | $^1$H-NMR (300 MHz, DMSO-d6, δ ppm): 7.36-7.52 (m, 2 H), 7.21-7.27 (m, 1 H), 7.14 (ddd, 1 H), 4.77-5.05 (m, 1 H), 3.96-4.26 (m, 1 H), 3.51-3.76 (m, 2 H), 2.68-3.24 (m, 2 H), 2.07-2.60 (m, 4 H), 1.62-1.86 (m, 1 H). MS (ESI Pos, 3.2KV, 25V, 350° C.): 263.16 (MH$^+$). m.p.: 123° C.-124° C. Yield: 68% (white powder). |
| 19 | 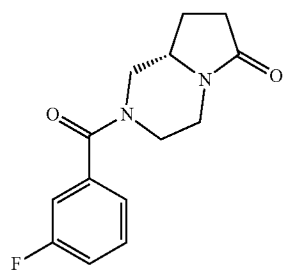 | (S)-2-(3-fluorobenzoyl) hexahydropyrrolo [1,2-a]pyrazin-6(7H)-one | $^1$H-NMR (300 MHz, DMSO-d6, δ ppm): 7.44-7.57 (m, 1 H), 7.18-7.35 (m, 3 H), 3.92-4.25 (m, 2 H), 3.86 (m, 1 H), 3.50-3.65 (m, 1 H), 2.61-2.94 (m, 3 H), 2.21-2.35 (m, 2 H), 2.00-2.21 (m, 1 H), 1.44-1.69 (m, 1 H). MS (ESI Pos, 3.2KV, 25V, 350° C.): 263.09 (MH$^+$). m.p.: 161° C.-162° C. Yield: 73% (white powder). |
| 20 | 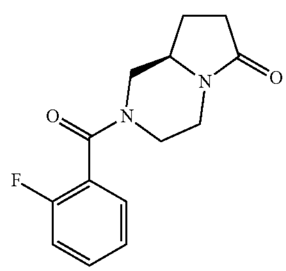 | (R)-2-(2-fluorobenzoyl) hexahydropyrrolo [1,2-a]pyrazin-6(7H)-one | $^1$H-NMR (300 MHz, DMSO-d6, δ ppm): 7.35-7.53 (m, 2 H), 7.21-7.32 (m, 1 H), 7.08-7.20 (m, 1 H), 4.76-5.05 (m, 1 H), 3.99-4.24 (m, 1 H), 3.51-3.76 (m, 2 H), 2.72-3.20 (m, 2 H), 2.07-2.59 (m, 4 H), 1.42-1.84 (m, 1 H). MS (ESI Pos, 3.2KV, 25V, 350° C.): 263.09 (MH$^+$). m.p.: 123° C.-124° C. Yield: 69% (white powder). |
| 21 | 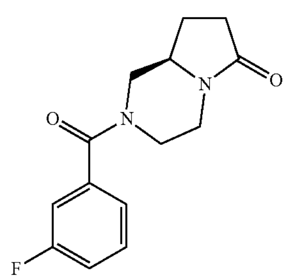 | (R)-2-(3-fluorobenzoyl) hexahydropyrrolo [1,2-a]pyrazin-6(7H)-one | $^1$H-NMR (300 MHz, DMSO-d6, δ ppm): 7.46-7.56 (m, 1 H), 7.20-7.33 (m, 3 H), 3.89-4.21 (m, 2 H), 3.76-3.88 (m, 1 H), 3.50-3.66 (m, 1 H), 2.62-2.95 (m, 3 H), 2.21-2.35 (m, 2 H), 2.03-2.21 (m, 1 H), 1.46-1.66 (m, 1 H). MS (ESI Pos, 3.2KV, 25V, 350° C.): 263.16 (MH$^+$). m.p.: 161° C.-162° C. Yield: 71% (white powder). |

Example 22

(S)-(−)-2-(3-Methylisoxazole-5-carbonyl)hexahydro-pyrrolo[1,2-a]pyrazin-6(7H)-one To a solution of 3-methyl-isoxazole-5-carboxylic acid (100 mg, 0.79 mmol) in $CH_3CN$ (10 ml), carbonyldiimidazole (140 mg, 0.87 mmol) was added at room temperature. After stirring for 1 hour, a solution of (S)-(−)-hexahydropyrrolo[1,2-a]pyrazin-6(7H)-one (compound of Description 5, 121 mg, 0.86 mmol) in $CH_3CN$ (2 ml) was added dropwise at room temperature. After stirring the solution for 20 hours, the solvent was removed under vacuum and the residue purified by flash chromatography (DCM/MeOH 95/5 respectively) to afford the title compound as an oil (160 mg, 82% yield).

$[\alpha]_D^{25}$=−26.70 (c=1, DCM).

$^1$H-NMR (300 MHz, DMSO-d6, δ ppm): 6.75 (s, 1 H), 4.24 (br. s., 2 H), 3.85-3.99 (m, 1 H), 3.46-3.73 (m, 1 H), 2.71-3.03 (m, 3 H), 2.31 (s, 3 H), 2.24-2.30 (m, 2 H), 2.07-2.24 (m, 1 H), 1.47-1.76 (m, 1 H).

MS (ESI Pos, 3.2 KV, 25V, 350° C.): 250.10 ($MH^+$).

Example 23

2-(2-Fluoro-benzenesulfonyl)-octahydro-pyrido[1,2-a]pyrazin-6-one

To a solution of octahydro-pyrido[1,2-a]pyrazin-6-one (compound of Description 12, 20 mg, 0.13 mmol) in DCM (1 ml), TEA (16 mg, 0.16 mmol) and a solution of 2-fluoro-benzenesulfonyl chloride (25 mg, 0.13 mmol) in $CH_3CN$ (1 ml) were added at 0° C. After stirring 3 hours at room temperature, the solvent was evaporated. The residue was partitioned between water and ethyl acetate. The organic layer was washed with brine, dried ($Na_2SO_4$) and evaporated under reduced pressure. The residue was purified by flash chromatography (from DCM to DCM/MeOH/32% $NH_4OH$ 95/5/0.5 respectively) to afford the title compound (18 mg, 44% yield).

$^1$H-NMR (300 MHz, $CDCl_3$, δ ppm): 7.87 (ddd, 1 H), 7.54-7.69 (m, 1 H), 7.32 (td, 1 H), 7.25 (ddd, 1 H), 4.77 (ddd, 1 H), 3.76-3.97 (m, 2 H), 3.42-3.61 (m, 1 H), 2.76 (td, 1 H), 2.57 (dddd, 1 H), 2.21-2.52 (m, 3 H), 1.96-2.13 (m, 1 H), 1.63-1.95 (m, 2 H), 1.37-1.53 (m, 1 H).

MS (ESI Pos, 3.2 KV, 25V, 350° C.): 313.05 ($MH^+$).

Example 24

2-p-Tolyl-tetrahydro-pyrrolo[1,2-a]pyrazine-1,6-dione

A mixture of tetrahydro-pyrrolo[1,2-a]pyrazine-1,6-dione (compound of Description 15, 150 mg, 0.97 mmol), p-tolyliodide (424 mg, 1.94 mmol), CuI (62 mg, 0.32 mmol) and $K_2CO_3$ (134 mg, 0.98 mmol) in dimethylformamide (6 ml) was refluxed for 2 hours. The solvent was removed under vacuum; the residue was triturated with ethyl acetate and after filtering off the insoluble material, the organic layer was washed with brine, dried ($Na_2SO_4$) and evaporated under vacuum. The residue was purified by flash chromatography (DCM/MeOH 95/5 respectively) to give the title compound as a light brown powder (70 mg, 30% yield).

m.p.: 115° C.-117° C.

$^1$H-NMR (300 MHz, $CDCl_3$, δ ppm): 7.22 (m, 2 H), 7.14 (m, 2 H), 4.31-4.41 (m, 1 H), 4.17 (dt, 1H), 3.82-3.93 (m, 1 H), 3.71 (dt, 1 H), 3.42 (ddd, 1 H), 2.45-2.61 (m, 3 H), 2.36 (s, 3 H), 2.19-2.36 (m, 1 H).

MS (ESI Pos, 3.2 KV, 25V, 350° C.): 245.19 ($MH^+$).

Pharmacological Methods

Pain Threshold Measurements

In all methods, paw mechanical sensitivity was determined using either the paw pressure test or the incapacitance test.

The paw pressure test utilizes a Randall & Selitto apparatus, exerting a force that increases at constant rate (32 g/s). The stimulus at which rats withdrawn the paw was evaluated before and at different times after treatment. Results represent the mean of mechanical thresholds expressed as grams. To avoid any possible damage to the animal paw the maximum applied force was fixed at 240 g.

The incapacitance test utilizes an incapacitance tester that provides an automatic assessment of anti-hyperalgesic potency by measuring the weight distribution on the two hind paws of tested animal The force exerted by each limb (measured in grams) is averaged over a user selectable period thus indicating any tendency for the animal to shift its weight from one side to another, hence providing a quantitative measurement of incapacitance.

1. Chemotherapy-Induced Neuropathy

Peripheral neuropathy is induced by repeated administration of vincristine, paclitaxel or oxaliplatin to adult male Sprague-Dawley rats (150-200 g, supplier Harlan).

The following protocols were used respectively:

Vincristine: the drug was injected by intravenous route at the dose of 150 μg/kg. The treatment was performed every 2 days, for 5 times, until a cumulative dose of 750 μg/kg was reached. Paw pressure test was performed 4 days after the last injection (Marchand F. et al. 2003, *Brain Res.* 980:117-120).

Paclitaxel: paclitaxel (PCT) neuropathy was induced by intraperitoneal administration of 0.5 mg/kg once a day, on days 1, 3, 5 and 8. Cumulative paclitaxel dose was 2 mg/kg. The pharmacological test was performed 14-18 days after the last paclitaxel injection (Polomano R. C. et al. 2001, *Pain* 94:293-304).

Oxaliplatin: 2.4 mg/kg were injected by intraperitoneal route for 5 consecutive days followed by 2 days suspension (one cicle). A total of 3 cycles was performed, reaching a cumulative dose of 36 mg/kg (Cavaletti G. 2001, *Eur. J. Cancer* 37:2457-2463). The test was performed 48 h after the last oxaliplatin injection.

2. Osteoarthritic Pain

Osteoarthritis was induced by a single administration of 2 mg (in a volume of 25 μl) of monosodium iodoacetate (MIA) into the left knee joint of anaesthetized rats (male adult Sprague Dawley rats, 150-200 g, supplier Harlan) (Fernihough J. 2004, *Pain* 112:83-93). This treatment induces the progressive degeneration of the joint and the development of hyperalgesia, mimicking at the histological and behavioral levels what observed in humans. Pharmacological test was performed 7 days after treatment.

3. Antiviral-Induced Neuropathy

Adult male Sprague Dawley rats (150-200 g, supplier Harlan) were treated by intravenous route with a single administration of 25 mg/kg of nucleoside reverse transcriptase inhibitors ddC (2',3'-dideoxycytidine) or d4T (2',3'-didehydro-3'-deoxythymidine). Administration of these anti-HIV drugs induced a marked allodynic response to a mechanical stimulus. The maximum reduction of the paw pressure threshold is developed between day 5 and day 10 after injection. The test was performed on day 10.

4. Streptozotocin-Induced Hyperalgesia

The administration to rodents of the pancreatic toxin streptozotocin (STZ) induces both mechanical and thermal hyperalgesia, possibly by mimicking diabetic neuropathy. Rats (male adult Sprague Dawley rats, 150-200 g, supplier Harlan) were injected intraperitoneally with 50 mg/kg of STZ and 21 days after toxin treatment were tested for mechanical hyperalgesia in the paw pressure test.

5. Resiniferatoxin-Induced Hyperalgesia

Intraperitoneal administration to the rat of resiniferatoxin (RTX), a super-agonist of vanilloid receptor type 1, rapidly depletes the neurotransmitter capsaicin from primary afferent terminals. This event leads to a neuronal damage which results in diminished thermal sensitivity and mechanical hyperalgesia, mimicking human postherpetic neuralgia.

Rats (male adult Sprague Dawley rats, 150-200 g, supplier Harlan) were injected i.p. with 200 ug/kg of RTX and after 3 weeks were tested for mechanical hyperalgesia in the paw pressure test.

Results

1. Chemotherapy-Induced Neuropathy

The effects of representative compounds of the invention on paclitaxel-induced hyperalgesia are reported in Table 4. Compounds of the invention significantly reduced mechanical hyperalgesia measured with the paw-pressure test.

TABLE 4

EFFECT OF COMPOUNDS OF THE INVENTION ON PACLITAXEL-INDUCED HYPERALGESIA IN THE RAT (PAW-PRESSURE TEST)

| | | Mechanical threshold (g) | | |
|---|---|---|---|---|
| | Before Treatment | After Treatment | | |
| Treatment (dose) | basal | 15 min | 30 min | 45 min |
| SALINE + vehicle | 59.0 ± 2.1 | 57.8 ± 2.9 | 60.2 ± 2.3 | 58.2 ± 2.1 |
| PCT + SALINE | 31.9 ± 2.6 | 28.6 ± 2.1 | 31.7 ± 2.3 | 30.6 ± 2.4 |
| PCT + example 3 (3 mg/kg i.v.) | 32.5 ± 3.1 | 45.6 ± 3.9** | 53.3 ± 2.7** | 46.2 ± 3.3** |
| PCT + Example 4 (3 mg/kg i.v.) | 31.9 ± 2.6 | 51.1 ± 2.4** | 55.8 ± 2.4** | 47.3 ± 2.9** |
| PCT + Example 6 (3 mg/kg i.v.) | 31.9 ± 1.9 | 49.4 ± 3.0** | 48.8 ± 2.8** | 40.7 ± 2.2* |
| PCT + Example 7 (3 mg/kg i.v.) | 29.3 ± 2.1 | 38.7 ± 2.2 | 47.6 ± 2.4* | 36.4 ± 2.5 |
| PCT + Example 8 (3 mg/kg i.v.) | 30.6 ± 2.6 | 42.2 ± 3.0* | 39.3 ± 3.2* | 37.5 ± 3.2 |
| PCT + Example 9 (3 mg/kg i.v.) | 29.2 ± 2.9 | 41.6 ± 3.6* | 44.5 ± 2.8** | 42.9 ± 4.3* |
| PCT + Example 11 (3 mg/kg i.v.) | 32.0 ± 2.1 | 45.3 ± 1.6** | 50.7 ± 2.3** | 48.4 ± 2.7** |
| PCT + Example 12 (3 mg/kg i.v.) | 31.4 ± 2.5 | 39.8 ± 3.7 | 41.5 ± 3.8* | 39.2 ± 4.4 |
| PCT + Example 13 (1 mg/kg i.v.) | 30.5 ± 2.2 | 35.6 ± 3.1 | 39.7 ± 2.4* | 34.8 ± 3.3 |
| PCT + Example 20 (3 mg/kg i.v.) | 31.3 ± 2.5 | 41.4 ± 2.3* | 45.7 ± 3.5** | 35.8 ± 3.0 |
| PCT + Example 21 (3 mg/kg i.v.) | 33.6 ± 2.8 | 40.9 ± 3.5 | 46.2 ± 4.3** | 37.6 ± 4.3 |
| PCT + Example 24 (3 mg/kg i.v.) | 30.5 ± 3.3 | 42.2 ± 2.6* | 43.4 ± 4.1* | 36.5 ± 4.2 |

Results from two separate experiments.
Results represent the mean ± S.E.M. of mechanical thresholds expressed as grams.
Each value represents the mean of 6-8 rats, except for saline (15-24 rats).
*$P < 0.05$ and
**$P < 0.01$ versus paclitaxel-vehicle treated rats.

In the vincristine and oxaliplatin-induced hyperalgesia models, compounds of the invention showed activity in the range 0.3-10 mg/kg p.o.

2. Osteoarthritic Pain

The effects of representative compounds of the invention on MIA-induced hyperalgesia are reported in Tables 5 and 6. Compounds of the invention significantly reduced mechanical hyperalgesia measured either with the paw-pressure test (Table 5) or the incapacitance test (Table 6).

TABLE 5

EFFECT OF COMPOUNDS OF THE INVENTION ON MIA-INDUCED HYPERALGESIA IN THE RAT (PAW-PRESSURE TEST)

| Treatment (dose) | Mechanical threshold (g) | | | |
|---|---|---|---|---|
| | Before Treatment | After Treatment | | |
| | basal | 15 min | 30 min | 45 min |
| SALINE + vehicle | 60.4 ± 3.1 | 58.5 ± 2.4 | 61.9 ± 3.3 | 63.0 ± 4.6 |
| MIA + vehicle | 20.8 ± 2.3 | 21.5 ± 2.3 | 23.5 ± 2.0 | 25.2 ± 3.4 |
| MIA + Example 3 (3 mg/kg i.v.) | 21.9 ± 1.9 | 61.3 ± 3.0** | 58.1 ± 3.7** | 49.2 ± 4.1** |
| MIA + Example 4 (3 mg/kg i.v.) | 23.1 ± 2.5 | 41.4 ± 3.1** | 53.0 ± 3.5** | 42.6 ± 3.2** |
| MIA + Example 8 (3 mg/kg i.v.) | 22.6 ± 2.0 | 59.4 ± 1.6** | 63.8 ± 2.6** | 50.2 ± 3.7** |

Results represent the mean ± S.E.M. of mechanical thresholds expressed as grams.
Each value represents the mean of 6 rats
*P < 0.05,
**P < 0.01 versus MIA-vehicle treated rats.

TABLE 6

EFFECT OF COMPOUNDS OF THE INVENTION ON MIA-INDUCED HYPERALGESIA IN THE RAT (INCAPACITANCE TEST)

| Treatment (dose) | Mechanical threshold (g) | | | |
|---|---|---|---|---|
| | Before Treatment | After Treatment | | |
| | basal | 15 min | 30 min | 45 min |
| SALINE + vehicle | 110.1 ± 6.3 | 106.3 ± 8.7 | 116.3 ± 9.3 | 103.8 ± 9.6 |
| MIA + vehicle | 46.7 ± 8.5 | 43.7 ± 9.2 | 42.9 ± 7.3 | 39.0 ± 7.6 |
| MIA + Example 3 (3 mg/kg i.v.) | 41.8 ± 6.0 | 106.9 ± 7.3** | 112.1 ± 8.5** | 81.8 ± 6.6** |
| MIA + Example 4 (3 mg/kg i.v.) | 41.4 ± 5.8 | 90.1 ± 8.2** | 96.2 ± 7.5** | 72.5 ± 7.2** |
| MIA + Example 8 (3 mg/kg i.v.) | 40.4 ± 8.2 | 119.0 ± 7.5** | 113.5 ± 6.6** | 72.9 ± 6.3** |

Results represent the mean ± S.E.M. of mechanical thresholds expressed as grams of the right paw.
Each value represents the mean of 6 rats.
*P < 0.05,
**P < 0.01 versus MIA-vehicle treated rats.

3. Other Chronic Pain Models

In the other chronic pain models, compounds of the invention showed activity in the range 0.3-10 mg/kg p.o.

The invention claimed is:
1. A compound of formula

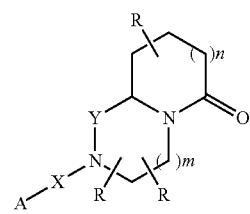

(I)

wherein:
each R group is, independently, H, $C_{1-6}$ alkyl, aryl, or $CF_3$;
Y is $CH_2$ or C=O;
X is $SO_2$,
m is 1,
n is 0,
A is a heterocyclic moiety, or a group of formula:

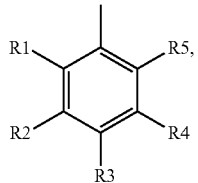

wherein:
R1, R2, R4 and R5 are, independently, H, halogen, $C_{1-6}$ alkyl, $C_{1-6}$ alkoxy, cyano, aryl, hydroxy, amino, $C_{1-6}$ alkylamino, di($C_{1-6}$ alkyl) amino, amino $C_{1-6}$ alkyl, ($C_{1-6}$ alkyl) amino $C_{1-6}$ alkyl, di($C_{1-6}$ alkyl) amino $C_{1-6}$ alkyl, carboxy or perhalo $C_{1-6}$ alkyl;

R3 is H, perhalo $C_{1-6}$ alkyl, halogen, $C_{1-6}$ alkyl, $C_{1-6}$ alkoxy, cyano, carboxy, hydroxy, $C_{1-6}$ alkylamino, di($C_{1-6}$ alkyl) amino, amino $C_{1-6}$ alkyl, ($C_{1-6}$ alkyl) amino $C_{1-6}$ alkyl, or di($C_{1-6}$ alkyl) amino $C_{1-6}$ alkyl;

or two adjacent groups chosen among R1, R2, R3, R4, or R5 may form a methylenedioxy or ethylenedioxy group, with the proviso that:

(i) when, simultaneously, Y is $CH_2$, and R1, R2, R4 and R5 are all hydrogen, then R3 is not H, F, Cl, $OCH_3$, or $CH_3$.

2. The compound of claim 1, wherein the alkyl groups of R1, R2, R3, R4, and R5 are independently $C_1$-$C_4$ alkyl groups.

3. The compound of claim 1, wherein the aryl groups of R1, R2, R3, R4, and R5 are independently $C_5$-$C_{10}$ aryl groups.

4. The compound of claim 1, wherein A is a saturated or unsaturated, single or fused heterocyclic ring, comprising one to four heteroatoms selected from the group consisting of oxygen, sulphur and nitrogen.

5. The compound of claim 1, wherein A is 2-pyridyl, 3-pyridyl, or 4-pyridyl.

6. The compound of claim 1, wherein one or two of R1, R2, R3, R4, and R5 are selected from the group consisting of hydrogen, halogen, cyano, trifluoromethyl, methyl, and methoxy and the remaining groups are hydrogen.

7. The compound of claim 1, wherein each R is independently H, Y is $CH_2$.

8. The compound of claim 1, selected from the group consisting of:

(S)-(−)-2-(2-fluorophenylsulfonyl)hexahydropyrrolo[1,2-a]pyrazin-6(7H)-one;
(S)-(−)-2-(3-fluorophenylsulfonyl)hexahydropyrrolo[1,2-a]pyrazin-6(7H)-one;
(R)-(+)-2-(2-fluorophenylsulfonyl)hexahydropyrrolo[1,2-a]pyrazin-6(7H)-one;
(R)-(+)-2-(3-fluorophenylsulfonyl)hexahydropyrrolo[1,2-a]pyrazin-6(7H)-one;
(R)-(+)-2-(3,4-difluorophenylsulfonyl)hexahydropyrrolo[1,2-a]pyrazin-6(7H)-one;
(R)-(+)-2-(o-tolylsulfonyl)hexahydropyrrolo[1,2-a]pyrazin-6(7H)-one;
(R)-(+)-2-(m-tolylsulfonyl)hexahydropyrrolo[1,2-a]pyrazin-6(7H)-one;
(R)-(+)-2-(2-(trifluoromethyl)phenylsulfonyl)hexahydropyrrolo[1,2-a]pyrazin-6(7H)-one;
(R)-(+)-2-(3-(trifluoromethyl)phenylsulfonyl)hexahydropyrrolo[1,2-a]pyrazin-6(7H)-one;
(R)-(+)-2-(4-(trifluoromethyl)phenylsulfonyl)hexahydropyrrolo[1,2-a]pyrazin-6(7H)-one;
(R)-2-(6-oxohexahydropyrrolo[1,2-a]pyrazin-2(1H)-ylsulfonyl)benzonitrile;
(R)-3-(6-oxohexahydropyrrolo[1,2-a]pyrazin-2(1H)-ylsulfonyl)benzonitrile;
(R)-(+)-4-(6-oxohexahydropyrrolo[1,2-a]pyrazin-2(1H)-ylsulfonyl)benzonitrile;
(R)-2-(2-methoxyphenylsulfonyl)hexahydropyrrolo[1,2-a]pyrazin-6(7H)-one;
(R)-2-(3-methoxyphenylsulfonyl)hexahydropyrrolo[1,2-a]pyrazin-6(7H)-one;
(R)-2-(pyridin-3-ylsulfonyl)hexahydropyrrolo[1,2-a]pyrazin-6(7H)-one; and
(R)-2-(pyridin-2-ylsulfonyl)hexahydropyrrolo[1,2-a]pyrazin-6(7H)-one.

9. A pharmaceutical composition comprising the compound of claim 1 and a pharmaceutically acceptable carrier.

10. A process for making the compound of claim 1, comprising reacting a compound of formula,

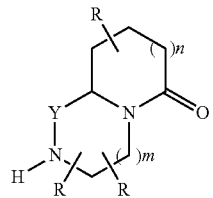

with a compound of formula

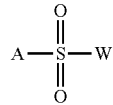

where W is halogen.

* * * * *